(12) United States Patent  
Ward et al.

(10) Patent No.: US 9,289,316 B2
(45) Date of Patent: Mar. 22, 2016

(54) QUASI-ACTIVE PROSTHETIC JOINT SYSTEM

(71) Applicant: SpringActive, Inc., Tempe, AZ (US)

(72) Inventors: Jeffrey A. Ward, Phoenix, AZ (US); Robert Holgate, Flagstaff, AZ (US); Kevin Hollander, Scottsdale, AZ (US)

(73) Assignee: SpringActive, Inc., Tempe, AZ (US)

( * ) Notice: Subject to any disclaimer, the term of this patent is extended or adjusted under 35 U.S.C. 154(b) by 0 days.

(21) Appl. No.: 14/269,103

(22) Filed: May 3, 2014

(65) Prior Publication Data
US 2014/0330393 A1 Nov. 6, 2014

Related U.S. Application Data

(60) Provisional application No. 61/819,049, filed on May 3, 2013.

(51) Int. Cl.
*A61F 2/66* (2006.01)
*A61F 2/68* (2006.01)
(Continued)

(52) U.S. Cl.
CPC .............. *A61F 2/6607* (2013.01); *A61F 2/66* (2013.01); *A61F 2/68* (2013.01); *A61F 2002/502* (2013.01); *A61F 2002/5003* (2013.01); *A61F 2002/503* (2013.01); *A61F 2002/5018* (2013.01); *A61F 2002/5021* (2013.01); *A61F 2002/5075* (2013.01); *A61F 2002/6664* (2013.01); *A61F 2002/6845* (2013.01); *A61F 2002/6854* (2013.01); *A61F 2002/701* (2013.01);
(Continued)

(58) Field of Classification Search
CPC ........... A61F 2/66; A61F 2/6607; A61F 2/68; A61F 2002/6845
See application file for complete search history.

(56) References Cited

U.S. PATENT DOCUMENTS 3,045,247 A 7/1962 Bair
6,436,149 B1 8/2002 Rincoe
(Continued)

FOREIGN PATENT DOCUMENTS

WO 2011096965 A2 8/2011

OTHER PUBLICATIONS

Mitchell et al., "Design and development of ankle-foot prosthesis with delayed release of plantarflexion", J. Rehabil. Res. Dev. 2013;50(3):409-22.

(Continued)

*Primary Examiner* — Marcia Watkins
(74) *Attorney, Agent, or Firm* — Robert D. Atkins; Patent Law Group: Atkins and Associates, P.C.

(57) ABSTRACT

A prosthetic joint device includes a foot portion and a main body pivotally coupled to the foot portion at a first joint. A first compliant member is coupled to the main body and foot portion. A first clutch is coupled to the first compliant member. An actuator is coupled to the first clutch to lock and unlock the first clutch and engage and disengage the first compliant member. A control system is coupled to the actuator to control the actuator based on a gait activity. The first clutch is locked to engage the first compliant member. A second compliant member is coupled to the main body and foot portion. A sensor is coupled to the prosthetic joint device to measure a physical state of the prosthetic joint device. The engagement and disengagement of the first compliant member is timed based on the physical state of the prosthetic joint device.

5 Claims, 28 Drawing Sheets

(51) Int. Cl.
| | |
|---|---|
| A61F 2/70 | (2006.01) |
| A61F 2/50 | (2006.01) |
| A61F 2/74 | (2006.01) |
| A61F 2/76 | (2006.01) |

(52) U.S. Cl.
CPC ....... *A61F2002/704* (2013.01); *A61F 2002/74* (2013.01); *A61F 2002/741* (2013.01); *A61F 2002/748* (2013.01); *A61F 2002/764* (2013.01); *A61F 2002/7625* (2013.01); *A61F 2002/7635* (2013.01); *A61F 2002/7645* (2013.01); *Y10T 29/49826* (2015.01)

(56) References Cited

U.S. PATENT DOCUMENTS

| | | | |
|---|---|---|---|
| 6,443,993 | B1 | 9/2002 | Koniuk |
| 7,431,737 | B2 | 10/2008 | Ragnarsdottir et al. |
| 7,811,333 | B2 | 10/2010 | Jonsson et al. |
| 7,985,265 | B2 | 7/2011 | Moser et al. |
| 7,992,849 | B2 | 8/2011 | Sugar et al. |
| 8,057,550 | B2 | 11/2011 | Clausen et al. |
| 8,202,325 | B2 | 6/2012 | Albrecht-Laatsch et al. |
| 8,322,695 | B2 | 12/2012 | Sugar et al. |
| 8,376,971 | B1 | 2/2013 | Herr et al. |
| 8,419,804 | B2 | 4/2013 | Herr et al. |
| 8,435,309 | B2 | 5/2013 | Gilbert et al. |
| 8,480,760 | B2 | 7/2013 | Hansen et al. |
| 8,500,825 | B2 | 8/2013 | Christensen et al. |
| 8,512,415 | B2 | 8/2013 | Herr et al. |
| 8,551,184 | B1 | 10/2013 | Herr |
| 8,696,764 | B2 | 4/2014 | Hansen et al. |
| 8,734,528 | B2 | 5/2014 | Herr et al. |
| 2005/0070834 | A1 | 3/2005 | Herr et al. |
| 2006/0173552 | A1 | 8/2006 | Roy |
| 2006/0249315 | A1 | 11/2006 | Herr et al. |
| 2007/0162152 | A1* | 7/2007 | Herr et al. ........................ 623/24 |
| 2008/0058668 | A1 | 3/2008 | Seyed Momen et al. |
| 2010/0161077 | A1 | 6/2010 | Boone et al. |
| 2010/0185301 | A1* | 7/2010 | Hansen et al. .................. 623/47 |
| 2012/0203359 | A1 | 8/2012 | Schimmels et al. |
| 2013/0006386 | A1 | 1/2013 | Hansen et al. |
| 2013/0046218 | A1 | 2/2013 | Wiggin et al. |
| 2013/0173022 | A1* | 7/2013 | Arabian et al. ................. 623/49 |
| 2013/0310979 | A1 | 11/2013 | Herr et al. |
| 2014/0088729 | A1 | 3/2014 | Herr et al. |
| 2014/0088730 | A1 | 3/2014 | Hansen et al. |

OTHER PUBLICATIONS

Bernardi, M. et al., (1995), "The Efficiency of Walking of Paraplegic Patients Using a Reciprocating Gait Orthosis," Spinal Cord 33(7): 409-415.
Boehler, Alexander W. et al., (2008), "Design, Implementation and Test Results of a Robust Control Algorithm for a Powered Ankle Foot Orthosis," IEEE International Conference on Robotics and Automation (ICRA), IEEE.
Hitt, Joseph et al., (2010), "Dismounted Soldier Biomechanical Power Regeneration Kit (SPaRK)," Proceedings of the 27th Army Science Conference, Orlando, FL.
Hitt, Joseph et al., (2010), "Bionic Running for Unilateral Transtibial Military Amputees," Proceedings of the 27th Army Science Conference, Orlando, FL.
Hollander, Kevin W. et al., (2005), "A Robotic "Jack Spring" for Ankle Gait Assistance," DETC2005-84492, ASME International Design Engineering Technical Conference (IDETC2005), Long Beach, CA, American Society of Mechanical Engineers.
Kawamoto, Hiroaki et al., (2003), "Power Assist Method for HAL-3 Estimating Operator's Intention Based on Motion Information," IEEE International Workshop on Robot and Human Interactive Communication, Millbrae, CA.
Kazerooni, H. et al., (2005), "On the Control of the Berkeley Lower Extremity Exoskeleton (BLEEX)," Proceedings of the 2005 IEEE International Conference on Robotics and Automation, Barcelona, Spain, Apr. 2005.
Norris, James A. et al., (2007), "Effect of Augmented Plantarflexion Power on Preferred Walking Speed and Economy in Young and Older Adults," Gait & Posture 25(4): 620-627.
Sawicki, Gregory S. et al., (2009), "Mechanics and Energetics of Incline Walking with Robotic Ankle Exoskeletons," Journal of Experimental Biology 212(1).
Sawicki, Gregory S. et al., (2009), "Powered Ankle Exoskeletons Reveal the Metabolic Cost of Plantar Flexor Mechanical Work During Walking with Longer Steps at Constant Step Frequency," Journal of Experimental Biology 212(1).
Sawicki, Gregory S. et al., (2009), "It Pays to Have a Spring in your Step," Exercise and Sport Sciences Reviews 37(3).
Sugar, Thomas G., (2002), "A Novel Selective Compliant Actuator," Mechatronics 12(9-10): 1157-1171.
Walsh, Conor James et al., "Development of a Lightweight, Under-Actuated Exoskeleton for Load-Carrying Augmentation," Proceedings of the 2006 IEEE International Conference on Robotics and Automation, Orlando, Florida, May 2006.
Walsh, Conor James et al., (2006), Biomimetic Design of an Under-Actuated Leg Exoskeleton for Load-Carrying Augmentation, Cambridge, MA, Massachusetts Inst of Tech, M.S.
Ward, Jeffrey et al., (2007), "Robotic Gait Trainer Reliability and Stroke Patient Case Study," IEEE 10th International Conference on Rehabilitation Robotics (ICORR), Holland.
Ward, Jeffrey et al., (2008), "Control Architectures for a Powered Ankle Foot Orthsosis," International Journal of Assistive Robotics and Mechatronics 9(2): 2-13.
Ward, Jeffrey et al., (2010), "Stroke Survivor Gait Adaptation and Performance After Training on a Powered Ankle Foot Orthosis," Proceedings of the IEEE International Conference on Robotics and Automation (ICRA), Anchorage, AK, IEEE.
Ward Jeffrey et al., (2011), "Using the Translational Potential Energy of Springs for Prosthetic Systems," IEEE Multi-conference on Systems and Control, Denver, CO, IEEE.
Hollander, Kevin W. et al., "Adjustable Robotic Tendon Using a 'Jack Spring'", Proceedings of the 2005 IEEE 9th International Conference on Rehabilitation Robotics. Jun. 28-Jul. 1, 2005, Chicago, IL, USA.
Czerniecki, Joseph, "Development of a Controlled Energy Storage and Release (CESR) Prosthetic Foot", Abstracts of Scientific Papers and Posters Presented at the Annual Meeting of the Association of Academic Physiatrists, Apr. 6-10, 2010.
Ficanha, Evandro et al., "A Two-Axis Cabel-Driven Ankle-Foot Mechanism", Robotics and Biomimetics, 1:17, 2014.
Morgenroth, David et al., "Knee Osteoarthritis in Lower Extremity Amputees: The effect of Prosthetic Foot Type on the Mechanical Loading Conditions Associated with this Common Secondary Disability", Abstracts of Scientific Papers and Posters Presented at the Annual Meeting of the Association of Academic Physiatrists, pp. 5-6, Apr. 6-10, 2010.
Vanderborght, Bram et al., "MACCEPA 2.0: Adjustable Compliant Actuator with Stiffening Characteristic for Energy Efficient Hopping", IEEE Conference on Robotics and Automation, pp. 1-6, Kobe, Japan, May 12-17, 2009.
Hollander, Kevin W. et al., "An Efficient Robotic Tendon for Gait Assistance", J. Biomech. Eng., 128(5):788-91, Oct. 2006.

* cited by examiner

QUASI-ACTIVE PROSTHETIC JOINT SYSTEM

CLAIM TO DOMESTIC PRIORITY

The present application claims the benefit of U.S. Provisional Application No. 61/819,049, filed May 3, 2013, which application is incorporated herein by reference.

FIELD OF THE INVENTION

The present invention relates in general to robotic devices and, more particularly, to active and compliant artificial joints and limbs including a system for controlled energy release.

BACKGROUND OF THE INVENTION

Human locomotion, such as walking and running, is commonly described in terms of gait. Gait is a cyclical or reoccurring pattern of leg and foot movement, rotations, and torques that creates locomotion. Due to the repetitive nature of gait, gait is typically analyzed in terms of percentages of a gait cycle. A gait cycle is defined for a single leg beginning with the initial contact of the foot with a surface such as the ground. The initial contact of the foot on the ground is referred to as a heel strike. The conclusion of a gait cycle occurs when the same foot makes a second heel strike. A gait cycle can be divided into two phases: stance phase and swing phase. Stance phase describes the part of the gait cycle where the foot is in contact with the ground. Stance phase begins with heel strike and ends when the toe of the same foot leaves the ground. Swing phase describes the part of the gait cycle where the foot is in the air and not in contact with the ground. Swing phase begins when the foot leaves contact with the ground and ends with the heel strike of the same foot. For walking gait speed, stance phase typically describes the first 60% of the gait cycle, while swing phase describes the remaining 40% of the gait cycle.

Prosthetic and orthotic devices help restore mobility to people who lack able-bodied motion or gait. Prosthetic devices are intended to replace the function or appearance of a missing limb and can return mobility to the wearer or user. Orthotic devices are intended to support or supplement an existing limb, by assisting with movement, reducing weight-bearing loads on the body, reducing pain, and controlling or restricting movement. Prosthetic and orthotic devices are available to replace or support various portions of the body. Lower limb prosthetic devices include, for example, the prosthetic foot, the foot-ankle prosthesis, the prosthetic knee joint, and the prosthetic hip joint. Lower limb orthotic devices include, for example, the foot orthoses, the ankle-foot orthoses, the knee-ankle-foot orthoses, and the knee orthoses. People who require a lower limb prosthesis or orthosis often expend more metabolic power to walk or move at the same speed as able-bodied individuals. One goal of lower limb prosthetic and orthotic devices is to help the user achieve a normal gait while reducing energy expended by the user.

The gait dynamics of a human joint can be described in terms of the position, velocity, moment, and power. During a typical walking gait cycle, the moment required from a human ankle reaches a maximum value of approximately 1.25 Newton meters per kilogram (N-m/kg) of body weight, while the typical velocity reaches a maximum of approximately 215 degrees per second, and the maximum power reaches approximately 3.5 Watts per kilogram (W/kg) of body weight. One goal of prosthetic and orthotic devices is to match the characteristics of able-bodied gait.

Prosthetic and orthotic devices can be divided into three groups, passive devices, active devices, and bionic devices. Passive lower limb prosthetics generally rely on compliant members, such as springs, to store and release energy. A spring is able to return only as much energy as is put into the spring, minus efficiency losses. Thus, the energy that is released by a spring in a passive device is limited to the energy that is put in by the user. Additionally, existing spring-based prosthetic ankles return the energy inefficiently to the user and are optimized for a single gait speed. As result, current prosthetic ankles can lack sufficient power return to produce normal gait. The user of a prosthetic must expend additional energy through recruiting other muscles and joints in a compensation strategy to maintain a functional gait. Therefore, passive prosthetic and orthotic designs are limited in capacity to reduce a user's metabolic energy expenditure while achieving a normal walking gait and performing other activities. Existing research has shown a 10-30% increase in metabolic cost for walking over able-bodied norms, depending on amputation level and gait speed.

Active devices differ from passive devices in that active devices employ a microprocessor and actuator to supply power to the device and to control the device. One type of active lower limb prosthetic device uses a microprocessor to control damping characteristics. Damping is typically performed with hydraulic valves and has the effect of converting energy into waste heat. Other active devices use a motor and drive transmission to control the orientation of the foot body relative to the shank body.

Fully active or bionic devices differ from active devices in that bionic devices employ a motor to supply power to the device and to control the device and add energy to the user. Current bionic devices face many design challenges. Some bionic device designs attempt to fully power knee or ankle gait. Bionic devices require larger motors, heavier and more robust drive-trains, larger and heavier batteries, struggle to provide enough power output for moderate gait activities.

Control systems for bionic devices are limited in capability to control the devices, because the systems require a signature gait move to occur before triggering a controller to switch gait activities, such as ascending or descending slopes or stairs. Further, bionic prostheses are limited to low or moderate power gait activities, because the power output necessary for high power gait activities such as running or jumping are not sustainable in a small portable system. One goal of bionic device designs is to increase efficiency of the active components and to build a lighter weight and more intuitively controlled system.

Another goal of prosthetic device designs is to perform more similarly to a human muscle during a variety of activities. Prosthetic devices are typically designed for a specific activity, such as walking. The majority of active compliant devices utilize a traditional rigid structure. The traditional rigid structure typically includes links powered by actuators such as electric motors or hydraulics. An activity-specific design strategy and traditional rigid structures may be suited for one specific activity, but the designs are limited in application and are not efficient beyond the intended activity. For example, devices designed for walking perform poorly for running, navigating uneven terrain, walking up and down inclines or stairs, or simply balancing while standing. Carrying heavy loads or transitioning from walking to running remains a challenge for users.

SUMMARY OF THE INVENTION

A need exists for prosthetic and orthotic devices that reduce the amount of power used to mimic the performance of a human ankle over a wide range of activities. Accordingly, in one embodiment, the present invention is a method of making a prosthetic joint device comprising the steps of providing a foot portion, providing a main body pivotally coupled to the foot portion at a first joint, providing a first compliant member coupled to the main body and foot portion, coupling a first clutch to the first compliant member, and providing an actuator coupled to the first clutch to engage and disengage the first clutch.

In another embodiment, the present invention is a method of controlling a prosthetic joint device comprising the steps of providing a foot portion, providing a main body coupled to the foot portion at a first joint, providing a first compliant member coupled to the main body and foot portion, providing an actuator coupled to the first compliant member and main body, and triggering the actuator to engage the first compliant member during a first gait phase.

In another embodiment, the present invention is a prosthetic joint device comprising a foot portion and a main body coupled to the foot portion at a first joint. A first compliant member is coupled to the main body and foot portion. A first clutch is coupled to the first compliant member. An actuator is coupled to the first clutch In another embodiment, the present invention is a prosthetic joint device comprising a foot portion and a main body coupled to the foot portion at a first joint. A first compliant member is coupled to the main body and foot portion. An actuator is coupled to the first compliant member.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

An active prosthetic device is generally described as a wearable robotic device controlled by a computerized control system. A fully-active prosthetic device employs an actuator to drive power into the movement of the device to strive for able-bodied motion. By contrast, the quasi-active prosthetic devices described herein employ one or more compliant elements, such as springs, together with an actuator to engage or disengage the spring in order to position the device and to engage spring power at the proper timing to better mimic able-bodied motion. Further, quasi-active prosthetic devices described herein may also incorporate a fully-active powered system together with the quasi-active design to provide both direct power and timed power release.

Figure 1A:
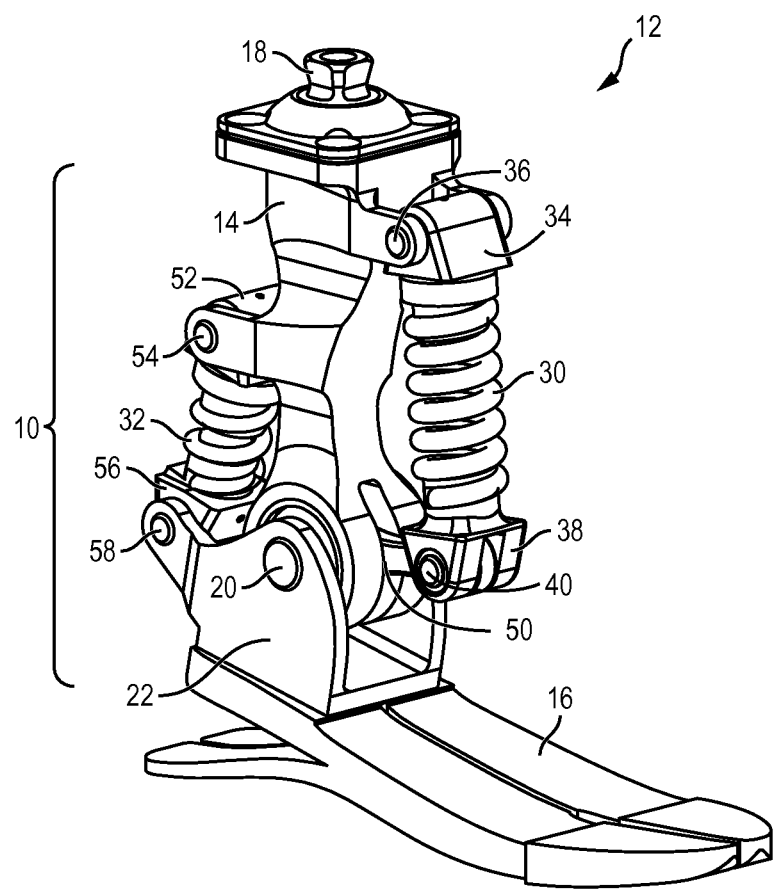
FIGS. 1a-1e illustrate a prosthetic ankle device including a quasi-active joint system.

FIGS. 1a-1e show a prosthetic ankle device including a quasi-active joint system. In FIG. 1a, a joint system 10 is implemented into a prosthetic ankle device 12. Prosthetic ankle device 12 operates as a quasi-active prosthetic device or wearable robotic device including active and passive components. Active components include actuators or motors. Passive components include compliant elements, such as springs, and damping elements. In one embodiment, prosthetic ankle device 12 is a below-the-knee prosthesis, which is also commonly known as a foot-ankle prosthesis or ankle prosthesis. In another embodiment, prosthetic ankle device 12 includes a robotic or prosthetic joint, such as a knee joint, hip joint, or other joint. Prosthetic ankle device 12 is worn by a user to replace a missing lower limb and restore the user's mobility and gait.

Prosthetic ankle device 12 includes a main body or pylon 14 and a foot portion or foot 16. Main body 14 includes a shank connector 18 configured to couple to a shank and socket, which fits onto a residual limb of a user. Foot 16 couples to main body 14 at an ankle joint 20 on foot mounting block 22. Foot mounting block 22 is rigidly coupled to foot 16. Foot mounting block 22 supports ankle joint 20. Ankle joint 20 comprises the primary joint for quasi-active joint system 10 and mimics a human ankle joint. Foot 16 rotates or pivots with respect to main body 14 at ankle joint 20. In one embodiment, ankle joint 20 includes a revolute or cylindrical joint and provides one degree of freedom by allowing rotation in the sagittal plane. In another embodiment, ankle joint 20 includes one or more joint types, or combination of joint types, such as revolute, prismatic, screw, spherical, planar, cylindrical, rigid, or other joint types, to provide one or more degrees of freedom at ankle joint 20.

Joint system 10 includes one or more compliant elements coupled to main body 14. In one embodiment, joint system 10 includes two or more compression springs, such as primary spring 30 and secondary spring 32. A primary spring 30 is coupled between main body 14 and foot 16 in a front or anterior position with respect to main body 14. A secondary spring 32 is coupled between main body 14 and foot 16 in a back or posterior position with respect to main body 14. Primary spring 30 and secondary spring 32 are disposed in parallel between main body 14 and foot 16 on opposing sides of main body 14 and ankle joint 20. Primary spring 30 and secondary spring 32 span ankle joint 20. Primary spring 30 is selected with a stiffness that is greater than a stiffness of secondary spring 32. Primary spring 30 is configured to absorb a substantial portion of the force of a gait step during stance phase and return the energy stored in primary spring 30 to the user during push off. Secondary spring 32 is configured to control the position of foot 16 during swing phase.

Primary spring 30 is coupled to main body 14 by spring mount 34 at a first end of primary spring 30. Spring mount 34 couples primary spring 30 to main body 14 at joint 36. Primary spring 30 is coupled to ankle joint 20 by spring mount 38 at a second end of primary spring 30 opposite the first end. Spring mount 38 couples primary spring 30 to ankle joint 20 at joint 40. In one embodiment, joints 36 and 40 include rigid joints. In another embodiment, joints 36 and 40 include revolute or cylindrical joints and permit primary spring 30 to pivot or rotate in the sagittal plane. Spring mount 38 is further coupled to ankle joint 20 by a clutch 50. Clutch 50 is pivotally coupled to ankle joint 20 such that clutch 50 rotates around ankle joint 20 in the sagittal plane. Thus, primary spring 30 is coupled to ankle joint 20 by clutch 50.

Secondary spring 32 is coupled to main body 14 by spring mount 52 at a first end of secondary spring 32. Spring mount 52 couples secondary spring 32 to main body 14 at joint 54. Secondary spring 32 is coupled to foot 16 by spring mount 56 at a second end of secondary spring 32 opposite the first end. Spring mount 56 couples secondary spring 32 to foot 16 at joint 58. Joint 58 is disposed on foot mounting block 22. In one embodiment, joints 54 and 58 include rigid joints. In another embodiment, joints 54 and 58 include revolute or cylindrical joints and permit secondary spring 32 to pivot or rotate in the sagittal plane. Therefore, joint system 10 is coupled between main body 14 and foot 16 with primary spring 30 and secondary spring 32 disposed on opposing sides of main body 14.

Figure 1B:
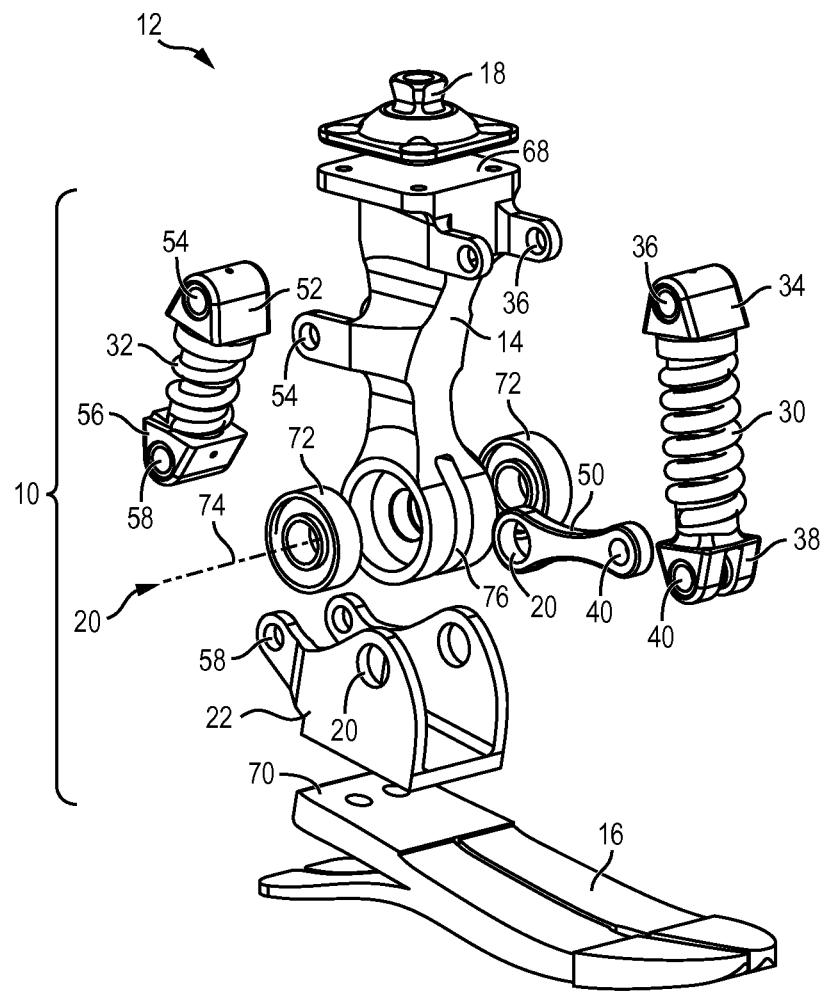

FIG. 1b shows the components of prosthetic ankle device 12 including joint system 10. Main body 14 comprises the primary shaft of joint system 10. Main body 14 is a rigid member that acts on primary spring 30 and secondary spring 32 to deflect the springs. Main body 14 includes metal, metal alloy, polymer, fiberglass, carbon fiber, a composite material, or a natural material. Main body 14 may include additional compliant or damping members. For example, main body 14 may comprise a pylon and spring or a pylon with a spring and damper. Shank connector 18 is mounted to main body 14 at joint 68. Shank connector 18 is coupled to or integrated with main body 14. In one embodiment, joint 68 is a rigid joint. Shank connector 18 is configured to couple to a user through additional links and fittings.

Foot 16 is a passive member and may include compliant features, such as a leaf spring. Foot 16 includes metal, metal alloy, polymer, fiberglass, carbon fiber, composite, or a natural material. Foot mounting block 22 is coupled to or integrated with foot 16. In one embodiment, foot mounting block 22 is coupled to foot 16 by a rigid joint 70. Foot mounting block 22 couples to main body 14 at ankle joint 20. Foot mounting block 22 couples to primary spring 30 at ankle joint 20 and to secondary spring 32 at joint 58.

Main body 14 interfaces with foot mounting block 22 through one or more bearings 72. Bearings 72 include radial bearings, ball bearings, thrust bearings, spherical or cylindrical ball bearings, or other bearing type. In one embodiment, bearings 72 include ball bearings. Main body 14, bearings 72, and foot mounting block 22 rotate about axis 74 of ankle joint 20. Axis 74 of ankle joint 20 is normal to the sagittal plane.

Primary spring 30 is disposed between main body 14 and foot 16 to compress and absorb energy as main body 14 rotates anteriorly over foot 16. Primary spring 30 is selected with a stiffness that supports the force generated during stance phase of gait. In one embodiment, primary spring 30 includes a helical or coil spring having a stiffness of 200,000 N/m. Primary spring 30 also bends with respect to the axis of the coil thereby operating as a torsional spring as well as a compression and tension spring. In another embodiment, primary spring 30 includes one or more helical or coil springs, torsional springs, leaf springs, or other compliant members. Additional linking members, such as a damping element, may be disposed in parallel or in series with primary spring 30. The operation of primary spring 30 is controlled by clutch 50.

Clutch 50 is a linking member that couples primary spring 30 to main body 14. Clutch 50 couples to joint 20 at a first end of clutch 50 and to joint 40 at a second end of clutch 50 opposite the first end. In one embodiment, clutch 50 fits within an opening 76 in main body 14 in order to align ankle joint 20 of clutch 50 with axis 74. Clutch 50 is rotationally coupled to foot mounting block 22 at ankle joint 20. Clutch 50 is further configured to alternately lock and unlock the rotation of clutch 50 with respect to foot mounting block 22. When clutch 50 is locked, clutch 50 is rigidly coupled to foot mounting block 22 causing primary spring 30 to engage. When clutch 50 is unlocked, clutch 50 is pivotally or rotationally coupled to foot mounting block 22 causing primary spring 30 to disengage.

Secondary spring 32 is oriented between main body 14 and foot 16 to control the plantarflexion and dorsiflexion of foot 16. Secondary spring 32 is configured to be engaged during the entire gait cycle and does not require a clutch. Secondary spring 32 is selected with a stiffness that is less than the stiffness of primary spring 30, but with a stiffness great enough to control foot 16. In one embodiment, secondary spring 32 includes a helical or coil spring having a stiffness of 45,000 N/m. Secondary spring 32 also bends with respect to the axis of the coil thereby operating as a torsional spring as well as a compression and tension spring. In another embodiment, secondary spring 32 includes one or more helical or coil springs, torsional springs, leaf springs, or other compliant members. Additional linking members, such as a damping element, may be disposed in parallel or in series with secondary spring 32.

Figure 1C:
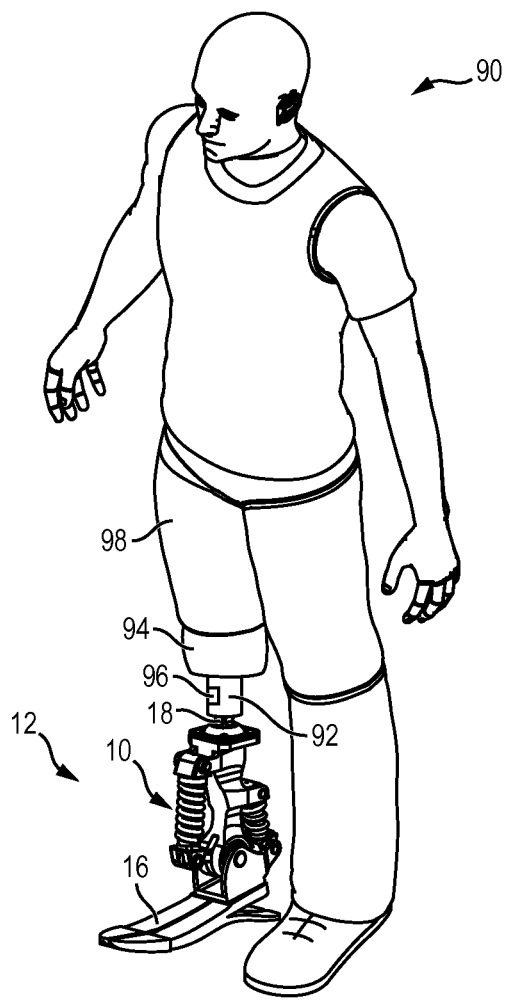

FIG. 1c shows prosthetic ankle device 12 including joint system 10 worn by a user 90. User 90 wears prosthetic ankle device 12, which is coupled to a shank 92 and a socket 94. Shank connector 18 couples main body 14 of prosthetic ankle device 12 to shank 92. Shank 92 couples to socket 94, which fits onto a residual limb of user 90.

Joint system 10 includes one or more active components, such as an actuator or motor, controlled by a computerized control system, such as a microprocessor with a motor controller. Joint system 10 implements a controller and an actuator to control the use of primary spring 30 and other components. The control system and actuator are incorporated into the structure of prosthetic ankle device 12. Alternatively, the control system is coupled to prosthetic ankle device 12 or coupled to user 90.

A sensor, plurality of sensors, or sensor system 96 is worn by user 90 and is coupled to the control system wirelessly or by wired connection. Sensor 96 is disposed on prosthetic ankle device 12, shank 92, foot 16, ankle joint 20, or other part of user 90. In one embodiment, sensor 96 is disposed on shank 92. In another embodiment, sensor 96 is worn on thigh 98 of user 90. A plurality of sensors 96 may be disposed on user 90. Sensor 96 includes an accelerometer, vibrometer, rate gyro, potentiometer, pressure transducer, force transducer or load cell, inclinometer, or other sensor. In one embodiment, a rate gyro is disposed on shank 92 and a potentiometer or ankle encoder is disposed on ankle joint 20. In another embodiment, sensor 96 includes a potentiometer is disposed on primary spring 30 or in proximity to primary spring 30 to measure force deflection. In another embodiment, sensor 96 includes a load cell disposed on main body 14, spring mounts for primary spring 30 or secondary spring 32, or any part of prosthetic ankle device 12. In yet another embodiment, sensor 96 includes a force-sensing resistor disposed on foot 16 of prosthetic ankle device 12. Sensor 96 detects a physical state of user 90 or prosthetic ankle device 12, such as a kinematic state, a loading state, or a kinematic state and a loading state. Measurements from sensor 96 are used by the control system to control joint system 10 of prosthetic ankle device 12.

Figure 1D:
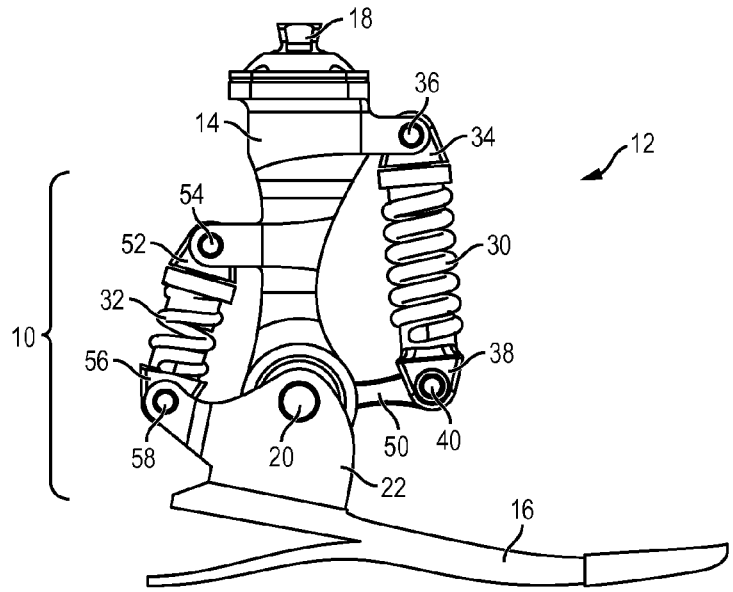

FIG. 1d shows a side view of prosthetic ankle device 12 including joint system 10. Primary spring 30 is coupled to a fixed point on main body 14, such as a rigid flange of main body 14. The position of joint 36 on main body 14 is selected according to the desired behavior of primary spring 30. The distance between joint 36 and joint 40 relative to main body 14 determines the linear extension and compression behavior of primary spring 30 as well as the torsional behavior as primary spring 30 bends.

Secondary spring 32 is coupled to a fixed point on main body 14, such as a rigid flange of main body 14. Secondary spring 32 is further coupled to a fixed point on foot mounting block 22, such as a rigid flange of foot mounting block 22. The positions of joint 54 on main body 14 and joint 58 on foot mounting block 22 are selected according to the desired behavior of secondary spring 32. The distance between joint 54 and joint 58 relative to main body 14 determines the linear extension and compression behavior of secondary spring 32 as well as the torsional behavior as secondary spring 32 bends.

Figure 1E:
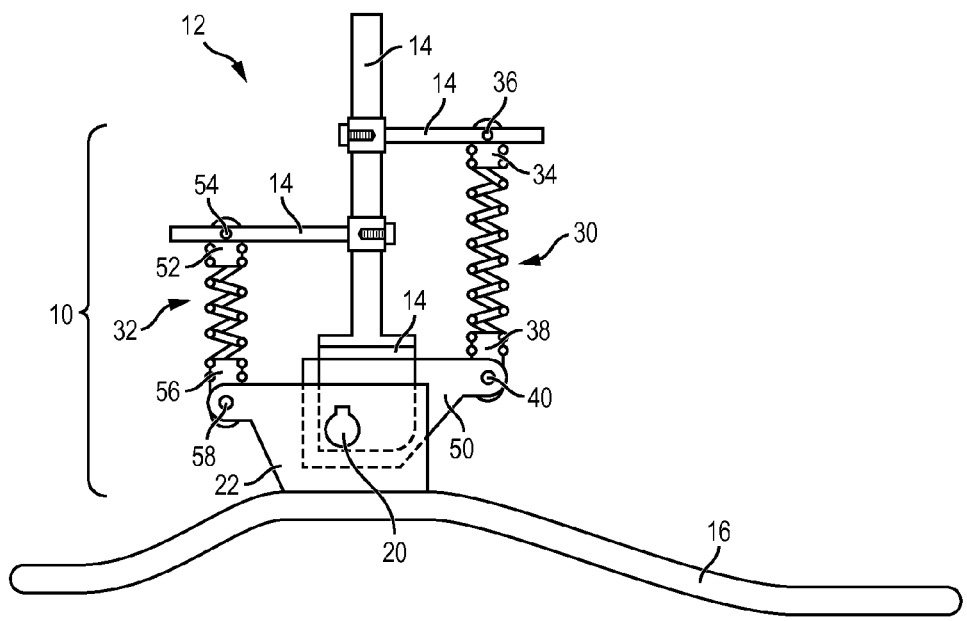

FIG. 1e shows a schematic of prosthetic ankle device 12 from FIGS. 1a-1d including joint system 10. Primary spring 30 and secondary spring 32 are disposed on opposing sides of ankle joint 20. In FIG. 1e, primary spring 30 is disposed anterior to main body 14 and secondary spring 32 is disposed posterior to main body 14. In an alternative embodiment, the positions of primary spring 30 and secondary spring 32 are reversed such that the posterior spring is the stiffer primary spring while the anterior spring is the softer secondary spring. In either configuration, the stiffer primary spring is the clutch-controlled spring. Main body 14, clutch 50, and foot mounting block 22 couple together at ankle joint 20. In FIG. 1e, ankle joint 20 is shown as a revolute joint configured to engage and disengage the rotation of clutch 50 with respect to foot mounting block 22. Main body 14 rotates around ankle joint 20. The rotation of main body 14 is controlled by secondary spring 32 and by primary spring 30, when primary spring 30 is engaged. Clutch 50 controls the involvement of primary spring 30 in joint system 10.

Figure 2A:
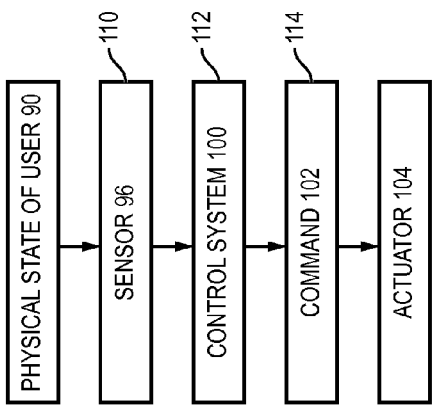
FIGS. 2a-2f illustrate schematic and graphical representations of quasi-active joint systems.

FIGS. 2a-2f show schematic and graphical representations of a quasi-active ankle device. FIG. 2a shows a method of controlling a joint system. Information from sensors 96 on user 90, actuator 104, and prosthetic ankle device 12 are input into control system. A control system 100 relates an input from sensor or sensors 96 and outputs a command 102 to actuator 104 in order to control clutch 50. Actuator 104 locks and unlocks clutch 50 in order to engage and disengage primary spring 30. By timing the engagement and disengagement of primary spring 30 at selected times during the gait cycle, the storage and return of energy in primary spring 30 is optimized according the physical state of user 90.

The method for controlling joint system 10 using control system 100 includes the steps of sensing 110 a physical state of user 90, processing 112 the sensed physical state and current actuator configuration or state using control system 100, and generating 114 a command 102 for actuator 104. During the step of sensing 110, sensor 96 detects a physical state of user 90, such as a kinematic state, a loading state, or a kinematic state and a loading state. Sensor 96 includes an accelerometer, vibrometer, rate gyro, potentiometer, pressure transducer, force transducer or load cell, inclinometer, or other sensor. The physical state measurement from sensor 96 is processed by control system 100.

During the step of processing 112 the signal from sensor 96, information about the user's gait is determined. The physical state measurement from sensor 96 is filtered and conditioned to obtain the user's speed, stride length, or percent of gait cycle. Other gait information may include current device ankle torque, ankle angle, foot center, and magnitude of pressure. The gait information is further processed to obtain a command 102 for actuator 104.

During the step of generating 114 a command 102, the processed physical state measurement is input into a reference function derived from able-bodied data. Command 102 is produced to engage or disengage clutch 50 and primary spring 30 in order to time the use of primary spring 30 to match data from one or more gait activities. Such activities include walking, running, traversing slopes or stairs, avoiding obstacles, and other similar activities. In one embodiment, the processed physical state measurement is compared with a recording or a calculation of able-bodied gait to match a desired gait activity. Command 102 is an output of control system 100 used to control actuator 104. Command 102 tells actuator 104 to engage or to disengage clutch 50, thereby engaging or disengaging primary spring 30. Command 102 also cycles engagement and disengagement of clutch 50 at a high rate in order to control energy release and obtain the necessary ankle moment.

Figure 2B:
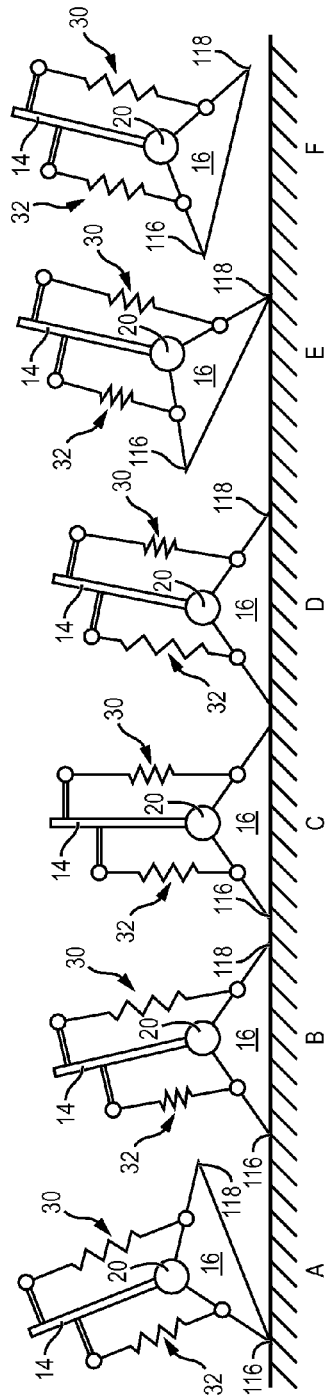

FIG. 2b show a schematic representation of prosthetic ankle device 12 through the different phases of a gait cycle. Position A represents heel strike at the beginning of stance phase for a human gait step. At heel strike, a heel 116 of foot 16 makes contact with the ground. Primary spring 30 and secondary spring 32 are at a free length, meaning the springs are not in tension or compression. Primary spring 30 is disengaged. Secondary spring 32 is not clutch-controlled, and thus, secondary spring 32 is engaged through the entire gait cycle. After heel strike, foot 16 begins to rotate downward, or in the direction of plantarflexion, toward the ground until foot 16 is flat on the ground. Secondary spring 32 absorbs part of the initial impact during heel strike to provide control during plantarflexion.

Position B represents the foot flat position of a gait step where foot 16 is in a planar flexed position. Secondary spring 32 is compressed. Primary spring 30 remains at free length until control system 100 locks clutch 50 to engage primary spring 30. The timing to engage primary spring 30 is selected according to the output desired from primary spring 30 during the push off phase. Primary spring 30 is engaged earlier in the gait cycle if a greater peak ankle torque or a greater ankle torque earlier in the gait cycle is desired. For example, primary spring 30 is engaged earlier if user is going down a slope or if more power is required for push off. In one embodiment, primary spring 30 is engaged at the foot flat position. After foot flat, main body 14 rotates at ankle joint 20 over foot 16.

Position C represents the mid-stance phase of gait. Where primary spring 30 was engaged prior to mid-stance, position C also represents a loading phase for primary spring 30. As main body 14 rolls over foot 16, primary spring 30 is compressed. Primary spring 30 absorbs and stores the energy caused by compressive loading of primary spring 30 during roll over. Secondary spring 32 is no longer compressed and is at free length. Main body 14 continues to roll over foot 16 until just before push off.

By contrast, without clutch 50, the loading of primary spring 30 begins at a fixed and unchangeable orientation. A neutral position of primary spring 30 is based on the free length and stiffness of primary spring 30 as compared with the free length and stiffness of secondary spring 32. If each stiffness is selected such that the neutral position occurs when foot 16 was perpendicular to main body 14, primary spring 30 would begin to compress only after main body 14 passed a neutral point at mid-stance. While mid-stance spring engagement provides proper gait dynamics for a single gait speed or slope condition, because engaging spring 30 later in the gait cycle results in less compression and thus, less energy stored in primary spring 30 and less power available later for push off. Different gait conditions like faster walking or slope walking require additional gait torque and power, and one fixed neutral position setting is not optimal for all walking conditions. In prosthetic ankle device 12, clutch 50 controls the engagement of primary spring 30 to provide the additional gait torque and power and provides better gait dynamics for varying gait conditions.

Position D represents the end of foot flat where the main body 14 has rolled over foot 16. Primary spring 30 is at peak compression for the gait cycle. Secondary spring 32 is in tension. As the foot is lifted at heel 116, primary spring 30 and secondary spring 32 begin to unload and force foot 16 into plantarflexion.

Position E represents the push off phase of a gait step. During push off, primary spring 30 releases the energy that was stored in the compression of primary spring 30 during the loading phases in the foot flat positions. As primary spring 30 unloads, foot 16 is forced into plantarflexion. At the end of push off, while toe 118 is in contact with the ground, foot 16 is in a plantarflexed position. Primary spring 30 and secondary spring 32 still hold some compression. At toe off, primary spring 30 tries to return to a free length position, which is the position of primary spring 30 at the point in time that primary spring 30 was engaged. In the present example, primary spring 30 returns to the plantarflexed position, because primary spring 30 was engaged at position B, which was an early foot flat phase of the gait step. Primary spring 30 is stiffer than secondary spring 32, such that primary spring 30 causes compression in secondary spring 32 as primary spring 30 attempts to return to free length. If primary spring 30 is engaged later in stance phase, primary spring 30 will return to a less plantarflexed position. Once toe 118 has lifted from the ground, clutch 50 is unlocked by control system 100 to disengage primary spring 30. Alternatively, the timing of primary spring 30 disengagement can be selected at any point of the gait cycle.

Position F represents the beginning of swing phase of a gait step. Entering swing phase, foot 16 is plantarflexed until primary spring 30 is disengaged. Once primary spring 30 is disengaged, secondary spring 32 is no longer held in compression by the stiffer primary spring 30. Secondary spring 32 releases the energy stored during compression to extend and push heel 116 downwards, thereby dorsiflexing foot 16. As a result of secondary spring 32 taking over, toe 118 is lifted out of the way for swing phase. Both primary spring 30 and secondary spring 32 return to free length and foot 16 is ready for the next gait cycle.

Figure 2C:
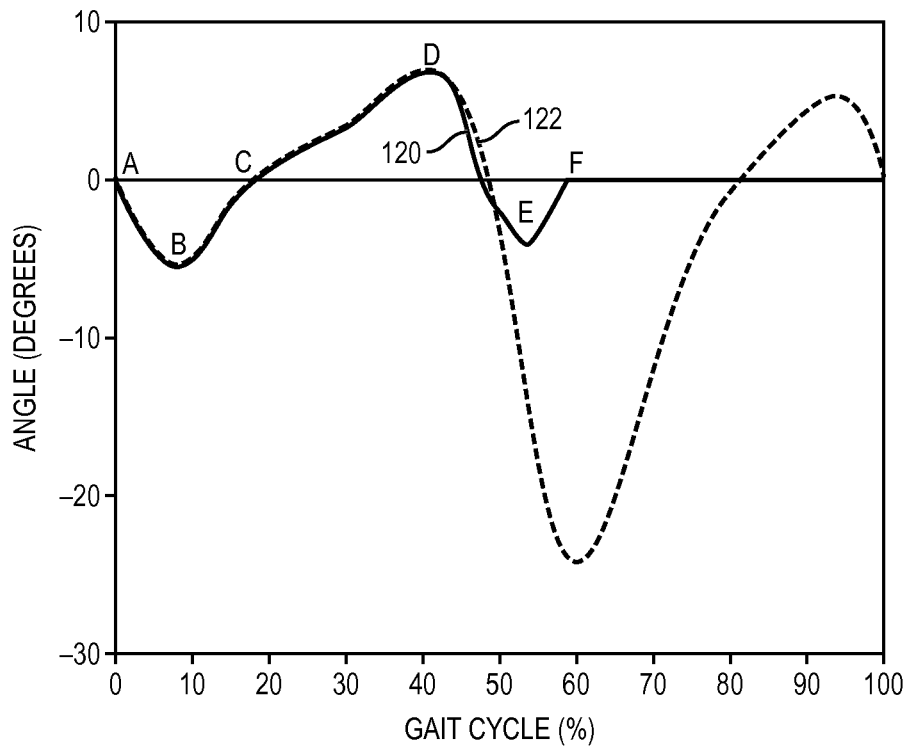

FIG. 2c shows a graphical representation of an ankle position throughout a gait cycle. Line 120 shows a representative angular position or angle of ankle prosthetic device 12. Points A-F on line 120 correlate to the ankle positions A-F shown in FIG. 2b. In FIG. 2c, position A or heel strike, is shown at the beginning of the gait cycle, which is plotted as 0% of the gait cycle. At point A on line 120, foot 16 is in a neutral position, which is plotted as zero degrees. Position B, which is an early foot flat phase of gait, is shown at approximately 10% of the gait cycle. At point B on line 120, foot 16 is in a plantarflexed position, which is plotted as approximately −5 degrees. Position C, which is mid-stance phase of gait, is shown at approximately 20% of the gait cycle. At point C on line 120, foot 16 is in a neutral position, which is plotted as zero degrees. Position D is at peak loading and peak dorsiflexion of the ankle joint and is shown at approximately 40% of the gait cycle. At point D on line 120, foot 16 is in a dorsiflexed position, which is plotted as approximately 8 degrees. Position E, which is the toe off phase of gait, is shown at approximately 55% of the gait cycle. At point E on line 120, foot 16 is in a plantarflexed position, which is plotted as approximately −4 degrees. Position F, which is swing phase of gait, is shown at approximately 60% of the gait cycle. At point F on line 120, foot 16 is in a neutral position, which is plotted as zero degrees.

Line 122 shows an ankle position for an able-bodied human ankle. Comparing line 120 for prosthetic ankle device 12 to the human data shown by line 122 shows that the position of prosthetic ankle device 12 closely matches able-bodied ankle position for approximately the first 55% of the gait cycle. Notably, line 120 shows that prosthetic ankle device 12 achieves plantarflexion at point E, which is the toe off phase of gait. The plantarflexion of foot 16 at point E indicates that primary spring 30 is engaged at the point of toe off. By contrast, simple passive devices do not achieve plantarflexion at toe off. By controlling the timing of primary spring 30 engagement according to the user's gait dynamics determined from sensor 96, the energy stored in primary spring 30 can be controlled for more efficient use during push off. Timing of the release or disengagement of primary spring 30 is used to controlling the rate of plantarflexion during push off.

Figure 2F:
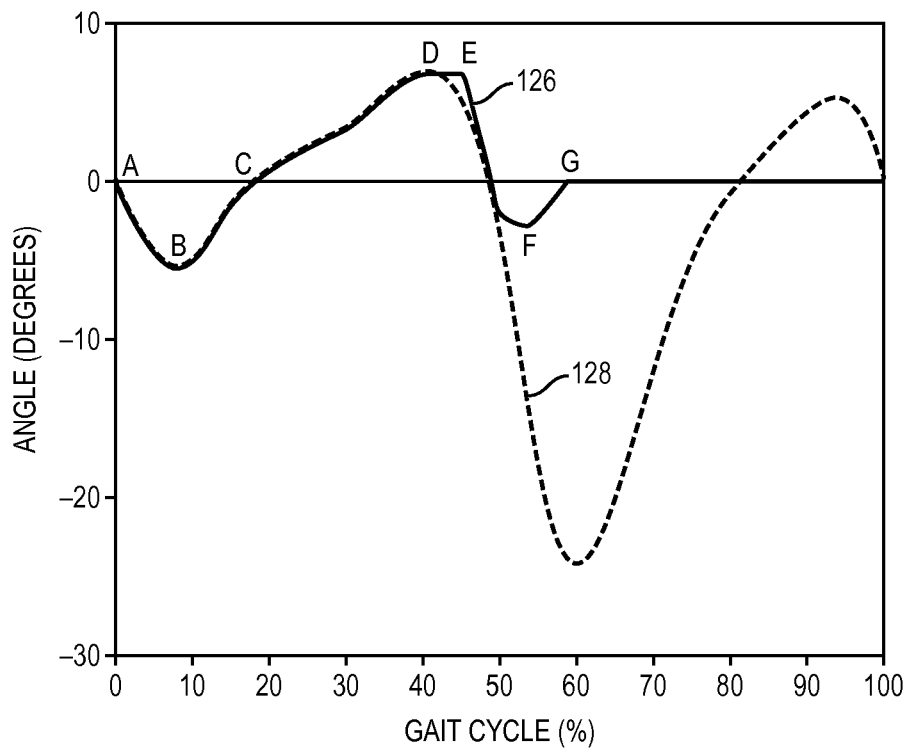
Figure 2D:
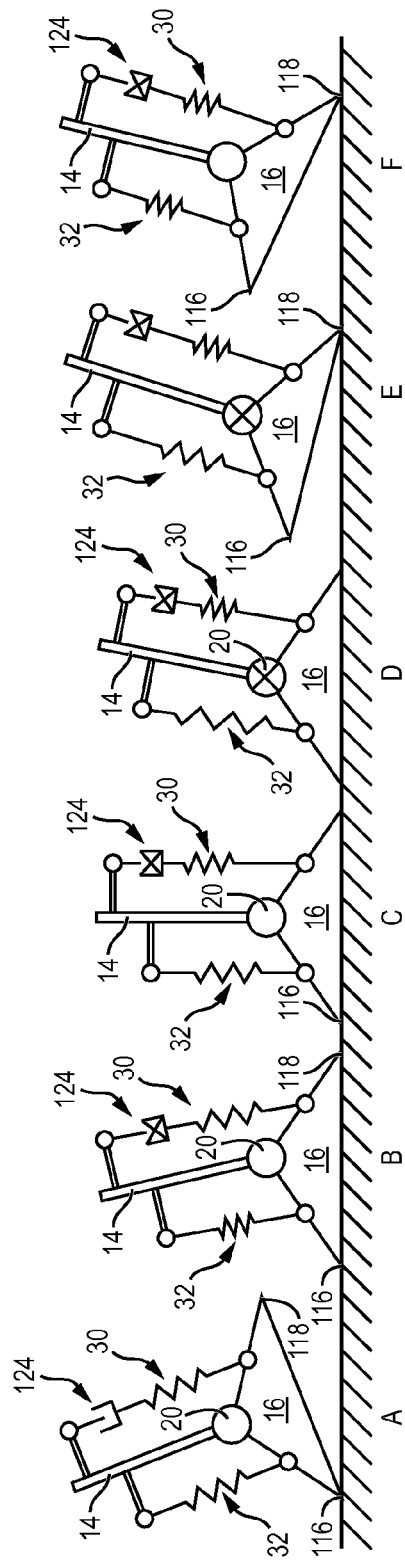

FIG. 2d shows a schematic representation of prosthetic ankle device 12 including a plurality of clutches operating through the different phases of a gait cycle. Joint system 10 includes a prismatic joint 124 disposed in series with primary spring 30 between main body 14 and foot 16. When prismatic joint 124 is unlocked, primary spring 30 is allowed to return or remain at free length. When prismatic joint 124 is locked, primary spring 30 is engaged. Joint system 10 further includes a lockable ankle joint 20. When ankle joint 20 is unlocked, main body 14 rotates relative to foot 16. When ankle joint 20 is locked, main body 14 is locked in a fixed position with respect to foot 16 such that main body 14 and foot 16 move together.

Position A in FIG. 2d represents heel strike at the beginning of stance phase for a human gait step. At heel strike, a heel 116 of foot 16 makes contact with the ground. Prismatic joint 124 and ankle joint 20 are unlocked. Primary spring 30 and secondary spring 32 are at a free length, meaning the springs are not in tension or compression. Primary spring 30 is disengaged. Secondary spring 32 is engaged and absorbs part of the initial impact during heel strike. After heel strike, foot 16 begins to rotate downward, or in the direction of plantarflexion, toward the ground until foot 16 is flat on the ground. Secondary spring 32 provides control during plantarflexion.

Position B in FIG. 2d represents the foot flat position of a gait step where foot 16 is in a planar flexed position. Ankle joint 20 is unlocked, and main body 14 is rotated posteriorly with respect to the foot in plantarflexion. Secondary spring 32 is compressed. Prismatic joint 124 is locked and primary spring 30 remains at free length until control system 100 locks clutch 50 to engage primary spring 30. After foot flat, main body 14 rotates at ankle joint 20 over foot 16.

Position C in FIG. 2d represents the mid-stance phase of gait. Ankle joint 20 is unlocked and allows main body 14 to roll over foot 16. Prismatic joint 124 is locked. The rotation of main body 14 over foot 16 compresses primary spring 30. Primary spring 30 absorbs and stores the energy caused by compressive loading of primary spring 30 during roll over. Secondary spring 32 is no longer compressed and is at free length. Ankle joint 20 is unlocked allowing main body 14 to continue to roll over foot 16. Main body 14 continues to roll over foot 16, further compressing primary spring 30, until ankle joint 20 is locked.

Position D in FIG. 2d represents the end of foot flat where the main body 14 has rolled over foot 16. Prismatic joint 124 is locked. Once ankle joint 20 is locked, main body 14 is fixed with respect to foot 16, and primary spring 30 is locked in compression. Primary spring 30 is at peak compression for the gait cycle. Secondary spring 32 is in tension.

Position E in FIG. 2d represents the heel off phase of a gait step, prior to toe off. Ankle joint 20 and prismatic joint 124 are locked. The compression in primary spring 30 is held by the locked position of joints 20 and 124. Secondary spring 32 is held in tension. As heel 116 lifts, foot 16 is held in position with respect to main body 14.

Position F in FIG. 2d represents the push off phase of a gait step. The release of ankle joint 20 is delayed until just after heel off. When ankle joint 20 is unlocked, primary spring 30 releases the energy that was stored in the compression of primary spring 30. Foot 16 is forced into plantarflexion. Primary spring 30 has a greater stiffness than secondary spring 32, thereby causing enough plantarflexion to compress secondary spring 32. Foot 16 remains in plantarflexion until prismatic joint 124 is unlocked. Prismatic joint 124 remains locked until just after toe off. Once prismatic joint 124 is unlocked, secondary spring 32 returns to free length and pushes heel 116 downwards and causing dorsiflexion in foot 16. Secondary spring 32 lifts toe 118 out of the way for swing phase. Both primary spring 30 and secondary spring 32 return to free length and the device is ready for the next gait cycle. Therefore, the lockable joints 20 and 124 control a timed release of energy stored in primary spring 30.

Figure 2E:
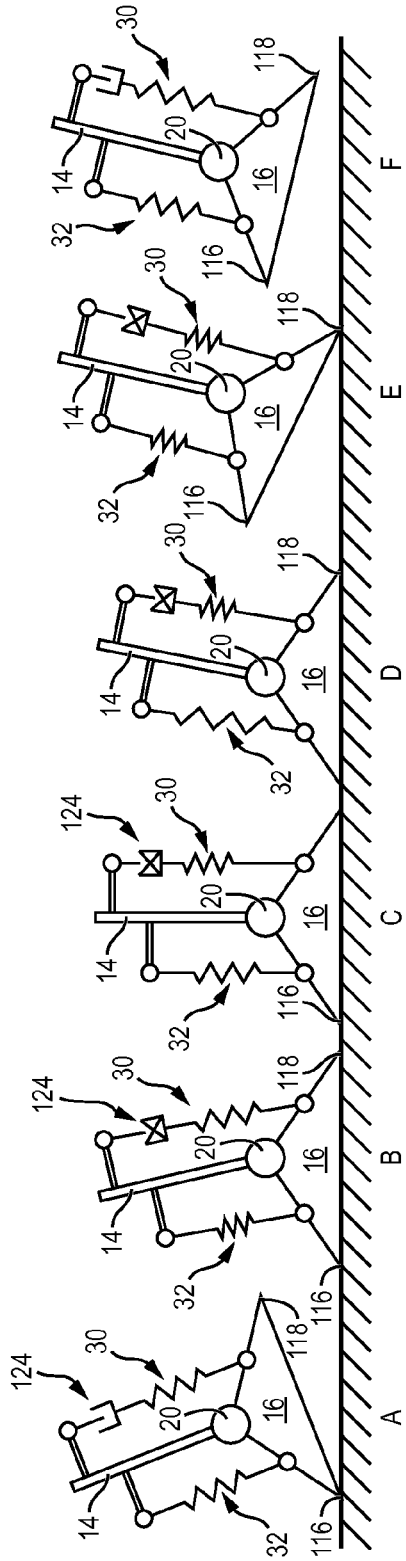

FIG. 2e shows a schematic representation of prosthetic ankle device 12 including a prismatic clutch operating through the different phases of a gait cycle. Joint system 10 includes a prismatic joint 124 disposed in series with primary spring 30 between main body 14 and foot 16. When prismatic joint 124 is unlocked, primary spring 30 is allowed to return or remain at free length. When prismatic joint 124 is locked, primary spring 30 is engaged. Prismatic joint 124 is locked and unlocked using a clutch. The clutch may include a hydraulic clutch, friction clutch, spring compensated friction clutch, a lever arm with spring, or other type of clutch.

Position A in FIG. 2e represents heel strike at the beginning of stance phase for a human gait step. At heel strike, a heel 116 of foot 16 makes contact with the ground. Prismatic joint 124 is unlocked. Primary spring 30 and secondary spring 32 are at a free length. Primary spring 30 is disengaged. Secondary spring 32 is engaged and absorbs part of the initial impact during heel strike. After heel strike, foot 16 begins to rotate in the direction of plantarflexion. Secondary spring 32 provides control during plantarflexion.

Position B in FIG. 2e represents the foot flat position of a gait step where foot 16 is in a planar flexed position. Main body 14 is rotated posteriorly with respect to the foot in plantarflexion. Secondary spring 32 is compressed. Prismatic joint 124 is locked and primary spring 30 remains at free length until control system 100 locks clutch 50 to engage primary spring 30. After foot flat, main body 14 rotates at ankle joint 20 over foot 16.

Position C in FIG. 2e represents the mid-stance phase of gait. Prismatic joint 124 is locked. The rotation of main body 14 over foot 16 compresses primary spring 30. Primary spring 30 absorbs and stores the energy caused by compressive loading of primary spring 30 during roll over. Secondary spring 32 is no longer compressed and is at free length.

Position D in FIG. 2e represents the end of foot flat where the main body 14 has rolled over foot 16. Prismatic joint 124 is locked and the rotation of main body 14 over foot 16 further compresses primary spring 30. Primary spring 30 is at peak compression for the gait cycle. Secondary spring 32 is in tension.

Position E in FIG. 2e represents the push off phase of a gait step. Prismatic joint 124 is locked. During push off, primary spring 30 releases the energy that was stored in the compression of primary spring 30. As primary spring 30 unloads, foot 16 is forced into plantarflexion. Primary spring 30 has a greater stiffness than secondary spring 32, thereby causing enough plantarflexion to compress secondary spring 32. Primary spring 30 and secondary spring 32 are in compression. At toe off, primary spring 30 tries to return to a free length position, which is the position of primary spring 30 at the point in time that primary spring 30 was engaged. At toe off, some plantarflexion occurs, depending on the differences in spring stiffness between primary spring 30 and secondary spring 32 and depending on the timing of primary spring 30 engagement.

Position F represents the beginning of swing phase of a gait step. Entering swing phase, foot 16 is plantarflexed until primary spring 30 is disengaged. Once prismatic joint 124 is unlocked, secondary spring 32 returns to free length and pushes heel 116 downwards and causing dorsiflexion in foot 16. Secondary spring 32 lifts toe 118 out of the way for swing phase. Both primary spring 30 and secondary spring 32 return to free length and the device is ready for the next gait cycle. Therefore, prismatic joint 124 allows a timed release of energy stored in primary spring 30.

FIG. 2f shows with respect to FIG. 2d, a graphical representation of an ankle position throughout a gait cycle with delayed energy release. Line 126 shows a representative angular position or angle of ankle prosthetic device 12 with a locking ankle joint 20. Points A-F on line 126 correlate to the ankle positions A-F shown in FIG. 2d. Position A or heel strike, is shown at the beginning of the gait cycle, which is plotted as 0% of the gait cycle. At point A on line 126, foot 16 is in a neutral position, which is plotted as zero degrees. Position B, which is an early foot flat phase of gait, is shown at approximately 10% of the gait cycle. At point B on line 126, foot 16 is in a plantarflexed position, which is plotted as approximately −5 degrees. Position C, which is mid-stance phase of gait, is shown at approximately 20% of the gait cycle. At point C on line 126, foot 16 is in a neutral position, which is plotted as zero degrees.

Position D represents peak loading and peak dorsiflexion of ankle joint 20 and is shown at approximately 40% of the gait cycle. The release of primary spring 30 is controlled by the timed unlocking of ankle joint 20. The beginning of plantarflexion is selected to optimize gait dynamics for a desired task. In FIG. 2f, beginning of plantarflexion is slightly delayed. At point D on line 126, foot 16 is in a dorsiflexed position, which is plotted as approximately 8 degrees, and begins to move into plantarflexion at about 45% of the gait cycle.

Position E represents the locked dorsiflexion position and delayed release of energy stored in primary spring 30. Ankle joint 20 is released from locked dorsiflexion at approximately 45%-50% of the gait cycle. Position F, which is the toe off phase of gait, is shown at approximately 55% of the gait cycle. At point F on line 126, foot 16 is in a plantarflexed position, which is plotted as approximately −4 degrees. Point G on line 126 in FIG. 2f illustrates the swing phase of gait, which is not shown in FIG. 2d. Swing phase begins at approximately 60% of the gait cycle, which is plotted as point G on line 126. Foot 16 is in a neutral position, which is plotted as zero degrees.

Line 128 shows an ankle position for an able-bodied human ankle. Comparing line 126 for prosthetic ankle device 12 shown in FIG. 2d to the human data shown by line 128 illustrates that the position of prosthetic ankle device 12 closely matches able-bodied ankle position for approximately the first 55% of the gait cycle. Notably, line 120 shows that prosthetic ankle device 12 achieves a delayed release from dorsiflexion at point D until point E. By controlling the timing of primary spring 30 engagement and the locking and releasing of ankle joint 20 according to the user's gait dynamics determined from sensor 96, the energy stored in primary spring 30 can be released at selected timing and selected release rates for more efficient use of the passive energy stored in primary spring 30.

Figure 3A:
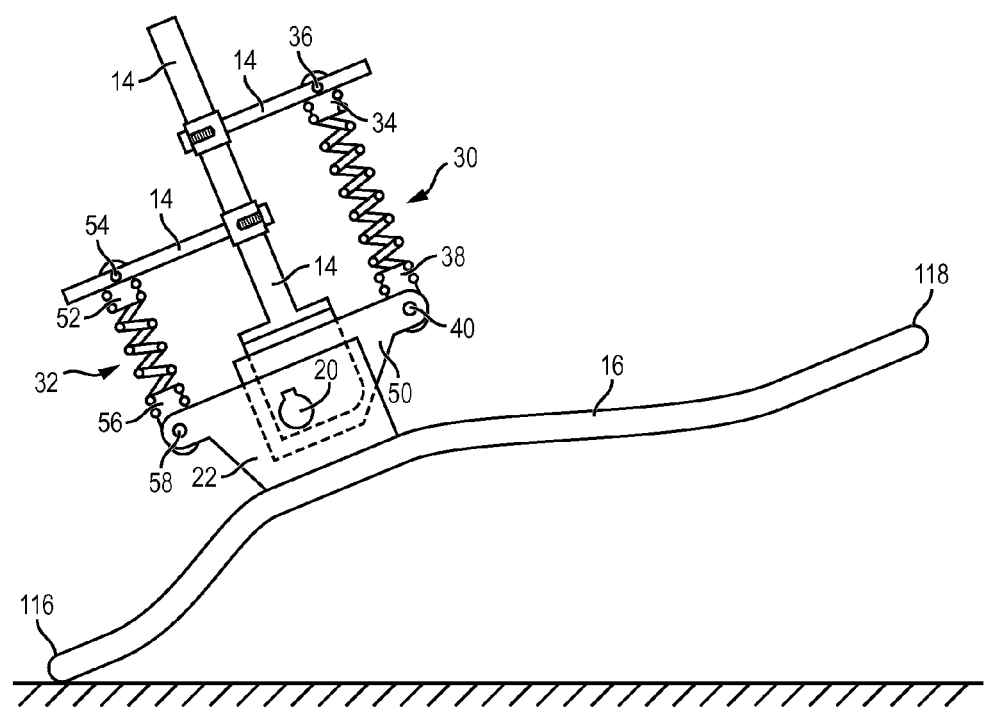
FIGS. 3a-3f illustrate a schematic representation of the operation of a prosthetic ankle device including a quasi-active joint system.

FIGS. 3a-3f show the operation of a quasi-active ankle device. FIG. 3a shows heel strike at the beginning of stance phase for a gait step with prosthetic ankle device 12. At heel strike, a heel 116 of foot 16 makes contact with the ground. Primary spring 30 and secondary spring 32 are at a free length. Clutch 50 is in an unlocked position. When clutch 50 is unlocked, clutch 50 rotates freely around ankle joint 20. Main body 14 also rotates freely with respect to foot mounting block 22 around ankle joint 20. Primary spring 30 and secondary spring 32 hold main body 14, clutch 50 in a neutral position with respect to foot 16. Therefore, clutch 50 and primary spring 30 remain in a neutral position with respect to main body 14, and primary spring 30 is effectively disengaged.

Secondary spring 32 is not clutch-controlled, and thus, secondary spring 32 is engaged through the entire gait cycle. Secondary spring 32 absorbs part of the initial impact during heel strike to provide control during plantarflexion. After heel strike, foot 16 begins to rotate downward, or in the direction of plantarflexion, toward the ground until foot 16 is flat on the ground.

Figure 3B:
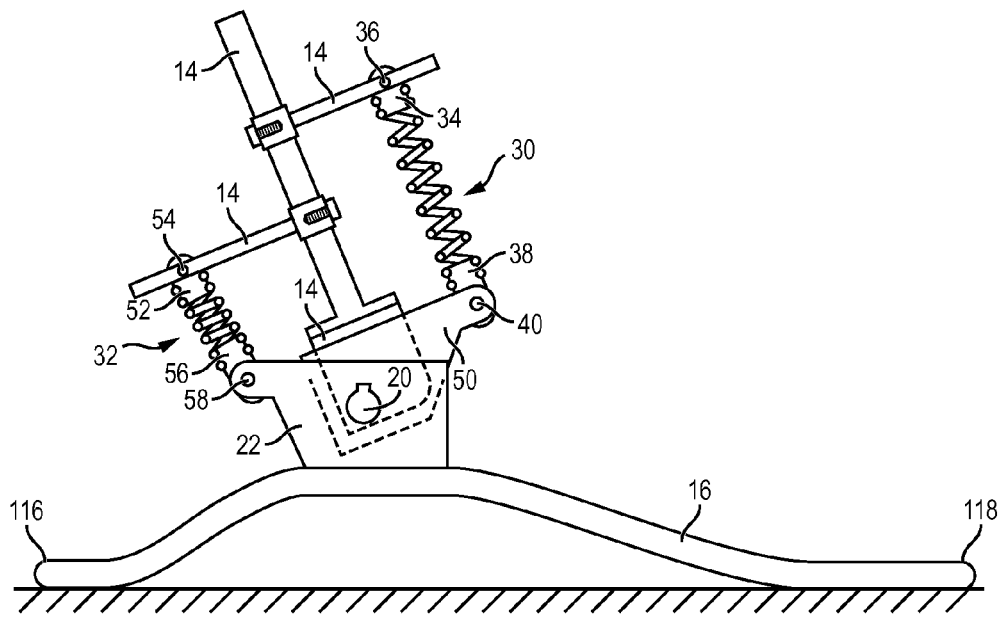

FIG. 3b shows the foot flat position of a gait step where foot 16 is in a planar flexed position. Foot 16 rotates into plantarflexion with respect to main body 14 and clutch 50. Clutch 50 is unlocked and permits rotation of clutch 50 around ankle joint 20. Primary spring 30 is disengaged and allows main body 14 and clutch 50 to rotate together. Secondary spring 32 is compressed. In one embodiment, joints 54 and 58 are fixed joints. The rotation of main body 14 causes a compressive force and a torsional or bending force on secondary spring 32. Control system 100 selects the point in the gait cycle at which to lock clutch 50 and engage primary spring 30. Clutch 50 is locked after toe 118 makes contact with the ground.

Figure 3C:
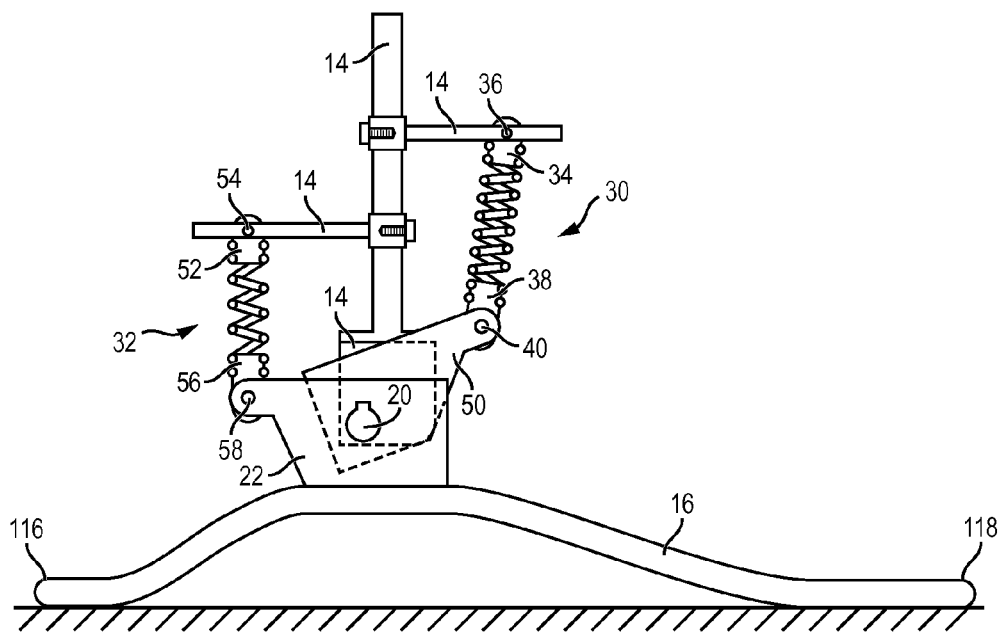

FIG. 3c shows mid-stance phase of gait. Clutch 50 is locked and is fixed in position with respect to ankle joint 20 and foot 16. Main body 14 remains free to rotate with respect to foot 16 around ankle joint 20. As main body 14 rolls over foot 16, primary spring 30 is compressed. Primary spring 30 absorbs and stores the energy caused by compressive loading of primary spring 30 during roll over. In one embodiment, joints 36 and 40 are fixed joints. The rotation of main body 14 causes a compressive force and a torsional or bending force on primary spring 30. When main body 14 reaches a neutral position with respect to foot 16, secondary spring 32 is no longer compressed and is at free length. Main body 14 continues to roll over foot 16 until just before push off.

Figure 3D:
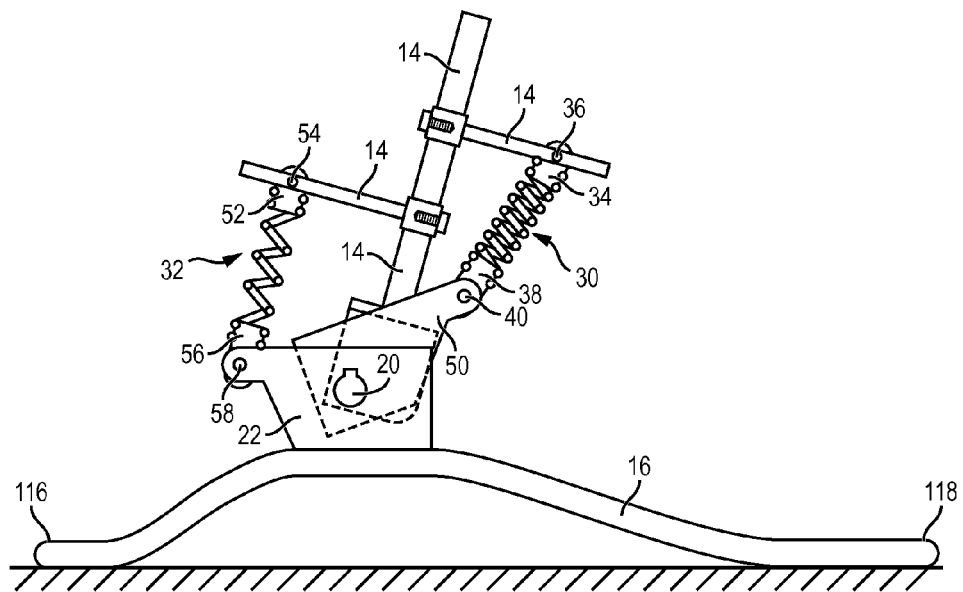

FIG. 3d shows the end of foot flat where the main body 14 has rolled over foot 16. Clutch 50 is locked and is fixed in position with respect to ankle joint 20 and foot 16. Primary spring 30 is at peak compression for the gait cycle. If joints 36 and 40 are fixed joints, primary spring 30 experiences a peak torsional force in addition to the compressive force. Secondary spring 32 is in tension. As the foot is lifted at heel 116, primary spring 30 and secondary spring 32 begin to unload and force foot 16 into plantarflexion.

Figure 3E:
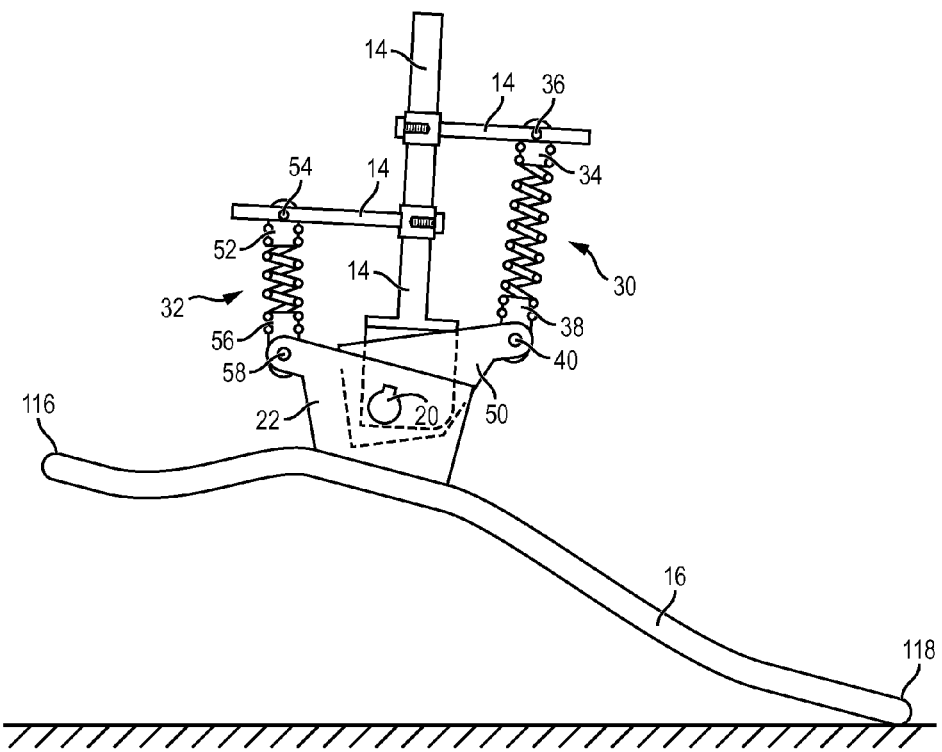

FIG. 3e shows the push off phase of a gait step. During push off, primary spring 30 releases the energy that was stored in the compression and torsional bending of primary spring 30 during the loading phases of gait. Clutch 50 remains locked and primary spring 30 pushes on main body 14 and foot 16. As primary spring 30 unloads, foot 16 is forced into plantarflexion. At the end of push off, while toe 118 is in contact with the ground, foot 16 is in a plantarflexed position. Primary spring 30 has a greater stiffness than secondary spring 32, thereby causing enough plantarflexion to compress secondary spring 32.

Figure 3F:
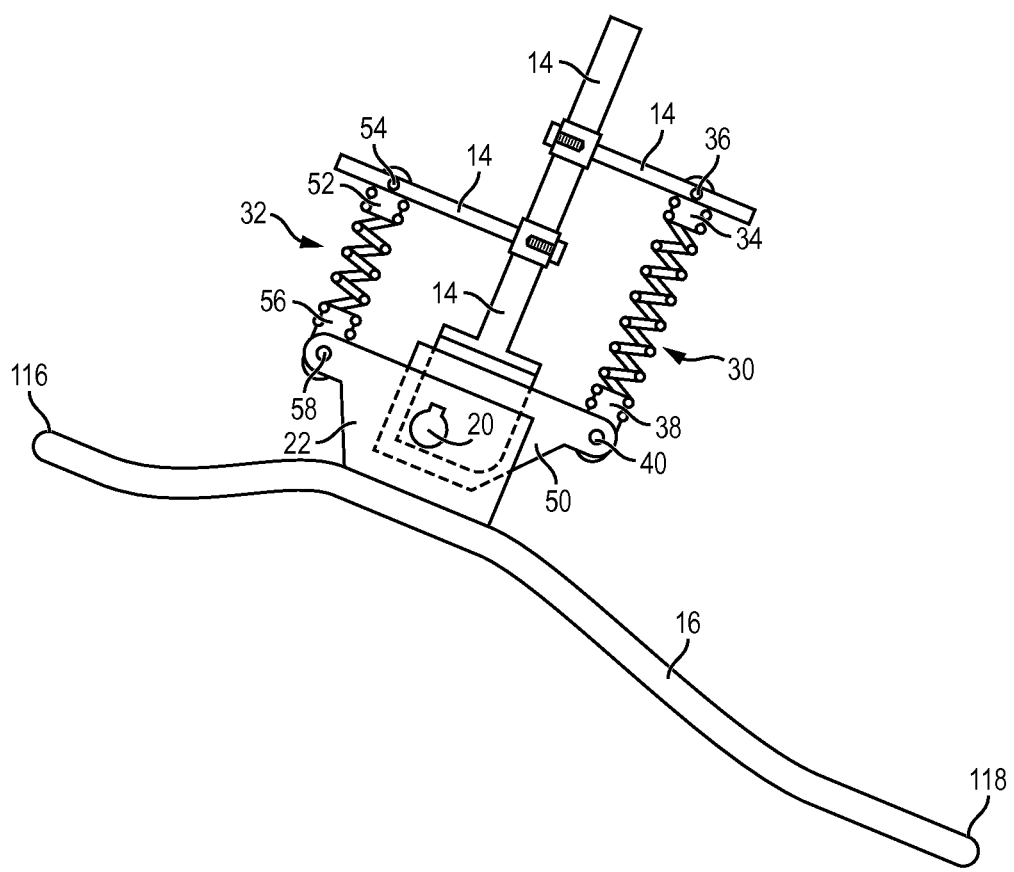

FIG. 3f shows the beginning of swing phase of a gait step. Clutch 50 is unlocked and primary spring 30 is disengaged. Clutch 50 is free to rotate with respect to foot 16 and main body 14. Once primary spring 30 is disengaged, secondary spring 32 is no longer held in compression by primary spring 30. Secondary spring 32 releases the energy stored during compression to extend and push heel 116 downwards, thereby dorsiflexing foot 16. Toe 118 is lifted out of the way for swing phase. Both primary spring 30 and secondary spring 32 return to free length and foot 16 is ready for the next gait cycle.

In another embodiment, secondary spring 32 is optional, and joint system 10 includes a single spring, such as primary spring 30. An actuator can be used to position foot 16 during swing phase, returning primary spring 30 to a neutral position or zero torque position. The position of foot 16 is actively controlled to modulate the storage and release of energy during the gait cycle. Therefore, the benefits of timed energy release and efficient use of passive energy is achieved in joint system 10.

Figure 4A:
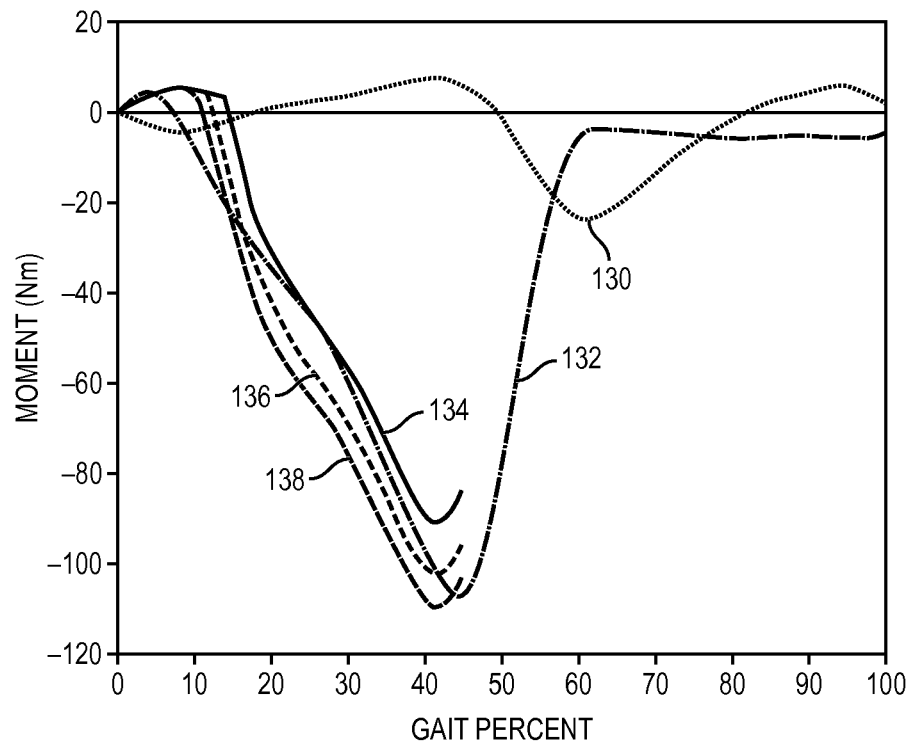
FIGS. 4a-4c illustrate graphs of moment curves for a prosthetic ankle device including a quasi-active joint system.
Figure 4B:
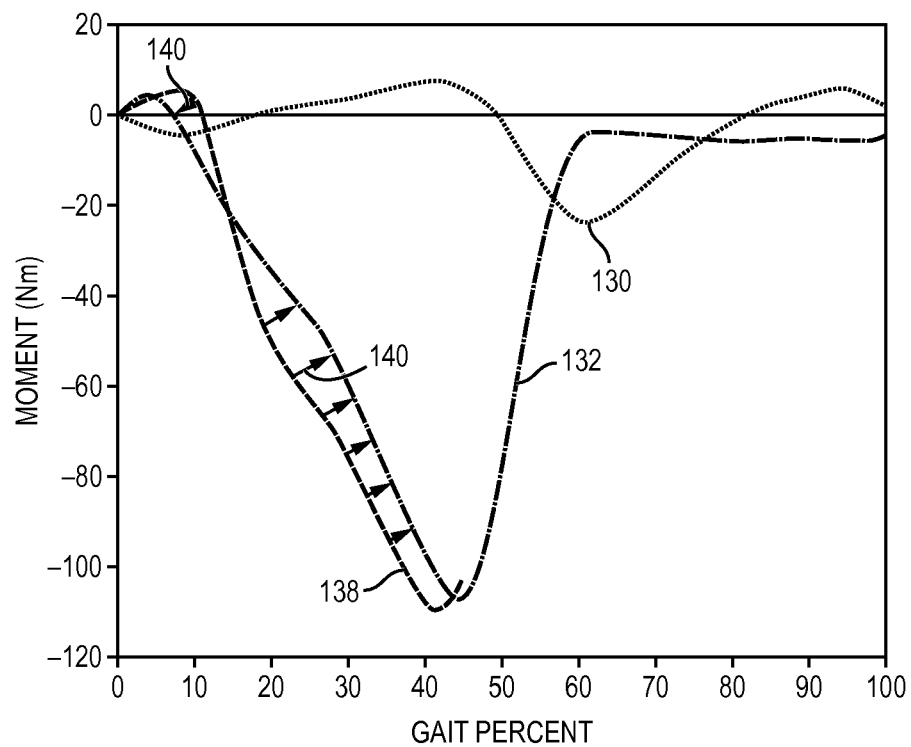

FIGS. 4a-4b show graphs of a moment curve for a quasi-active ankle device. FIG. 4a shows moment curves for a prosthetic ankle device 12 similar to the embodiment of FIG. 1a-1e. Line 130 shows an ankle position for an able-bodied human ankle. Line 132 shows an ankle moment curve for an able-bodied human ankle. Stance phase includes the first 60% of the gait cycle, while swing phase includes the remaining 40% of the gait cycle. Lines 134, 136, and 138 show moment loading curves for prosthetic ankle device 12. Lines 134, 136, and 138 depict the effect of varying the timing of the engagement of primary spring 30. The graph assumes constant spring stiffness. Line 134 shows a moment loading curve for prosthetic ankle device 12 where primary spring 30 of joint system 10 is engaged at 14% of the gait cycle. Line 136 shows a moment curve where primary spring 30 is engaged at 12% of the gait cycle. Comparing lines 134 and 136, the moment produced by prosthetic ankle device 12 is greater when primary spring 30 is engaged earlier in stance phase. Line 138 shows a moment curve where primary spring 30 is engaged at 9% of the gait cycle. The moment produced by prosthetic ankle device 12 at 9% engagement is greater than the moments at 12% and 14% engagement and the moment of an able-bodied ankle. Therefore, the timing of engagement of primary spring 30 affects the loading profile for prosthetic ankle device 12.

FIG. 4b shows a moment curve for a prosthetic ankle device 12 similar to the embodiment of FIGS. 1a-1e. Line 130 shows an ankle position for an able-bodied human ankle. Line 132 shows an ankle moment curve for an able-bodied human ankle. Line 138 shows a moment curve where primary spring 30 is engaged at 9% of the gait cycle. The effect of engaging primary spring 30 earlier in the gait cycle is that prosthetic ankle device 12 feels stiffer to user 90, because torque begins to build earlier in the gait cycle and excess torque can build up. The difference between an able-bodied moment, line 132, and a primary spring 30 engaged early in the gait cycle is shown by area 140. Area 140 depicts the excess moment or torque produced by prosthetic ankle device 12. In the case that the system builds up too much torque, energy is released at a controlled rate to dissipate some of the energy stored in primary spring 30. The energy is released by pulsing clutch 50, controlled damping, or by another method of dissipating energy stored in primary spring 30. Energy is released from primary spring 30 in order to better simulate the moment curve of prosthetic ankle device 12 with an able-bodied moment, line 132. Therefore, clutch 50 is used to control the moment loading curve of prosthetic ankle device 12 by releasing part of the energy stored in primary spring 30 at proper timing during the gait cycle.

Figure 4C:
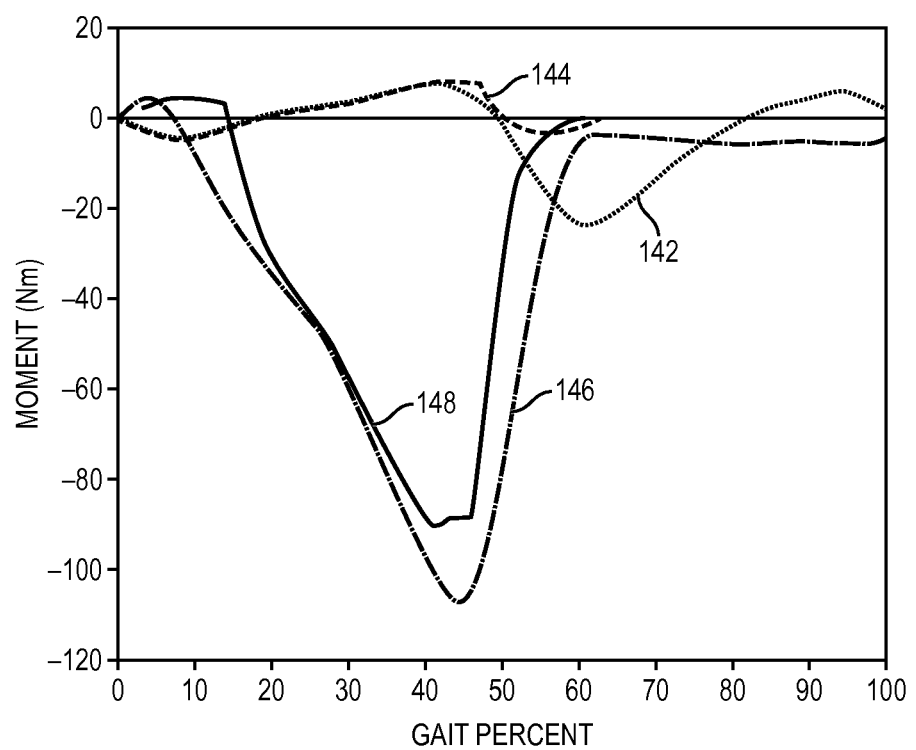

FIG. 4c shows a moment curve for a prosthetic ankle device 12 similar to the embodiment of FIG. 2d. Line 142 shows an ankle position curve for an able-bodied human ankle. Line 144 shows an ankle position curve for prosthetic ankle device 12. Line 144 shows that prosthetic ankle device 12 achieves a delayed transition into plantarflexion, which begins at approximately 45% of the gait cycle. Ankle joint 20 is unlocked and primary spring 30 releases. The timing of unlocking ankle joint 20 is selected to delay plantarflexion.

Line 146 shows an ankle moment curve for an able-bodied human ankle. Line 148 shows a moment curve where primary spring 30 is engaged at 14% of the gait cycle. The timing of engagement and disengagement of primary spring 30 affects the loading profile. In order to match the moment of prosthetic ankle device 12 to able-bodied data, the release of primary spring 30 is controlled. By locking ankle joint 20, foot 16 is locked in a dorsiflexed position until the proper push-off timing is achieved. When ankle joint 20 is unlocked, the stored energy in primary spring 30 releases to impart a delayed plantarflexion moment on foot 16. The rate of release of energy in primary spring 30 is also controlled by pulsing a clutch, damping, or by another method of dissipating energy stored in primary spring 30.

Figure 5A:
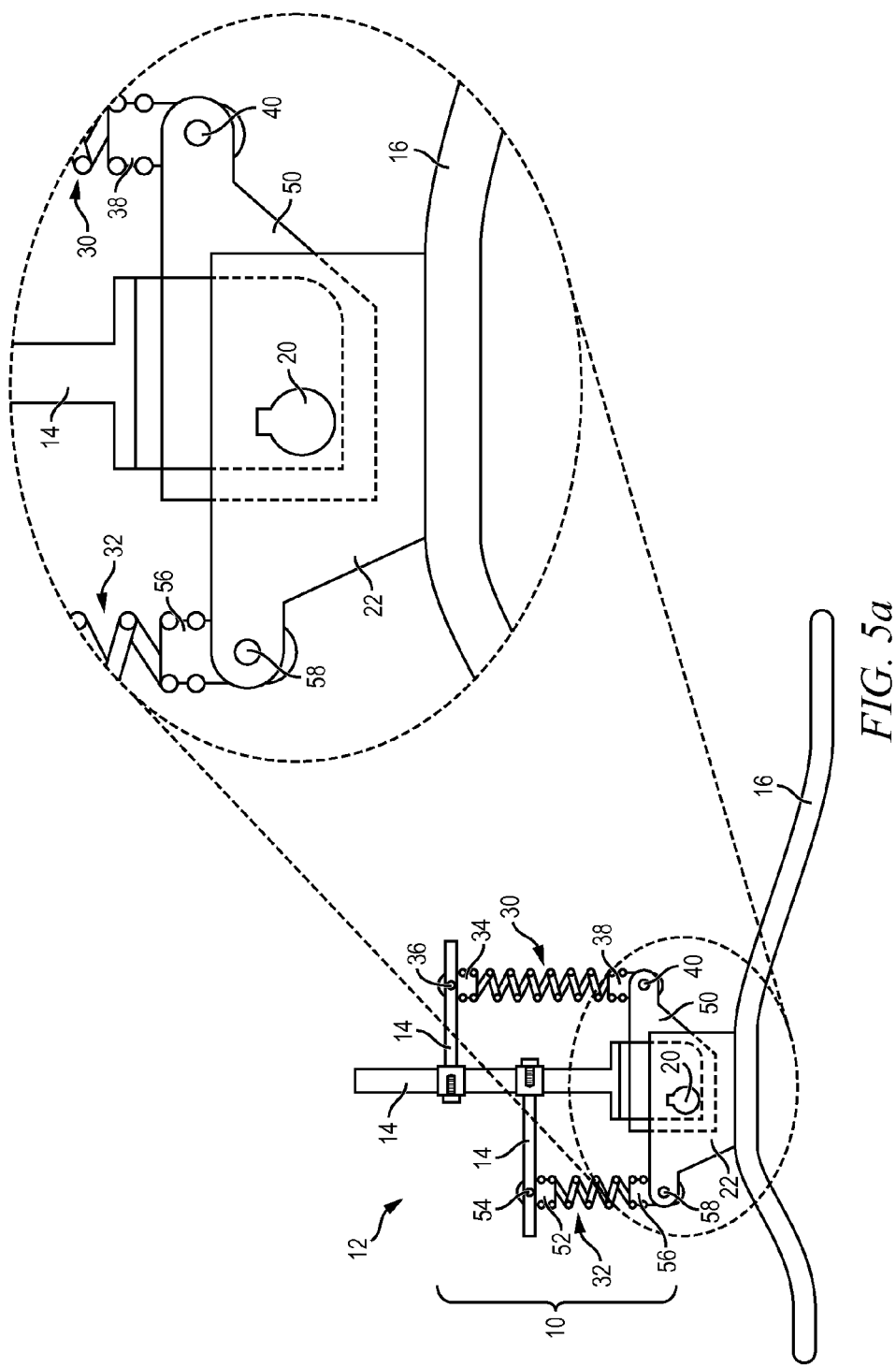
FIGS. 5a-5d illustrate alternative clutch systems for a quasi-active ankle device.

FIGS. 5a-5d show clutch systems for a quasi-active ankle device. FIG. 5a shows an embodiment of clutch 50. Clutch 50 may include friction pads, compressive members, or other clutch systems. Clutch 50 interfaces with main body 14 and foot mounting block 22 at ankle joint 20. Clutch 50 locks and unlocks in order to engage and disengage primary spring 30. Joint system 10 may further include additional clutch systems. In one embodiment, joint system 10 includes a clutch for locking main body 14 with respect to ankle joint 20.

Figure 5B:
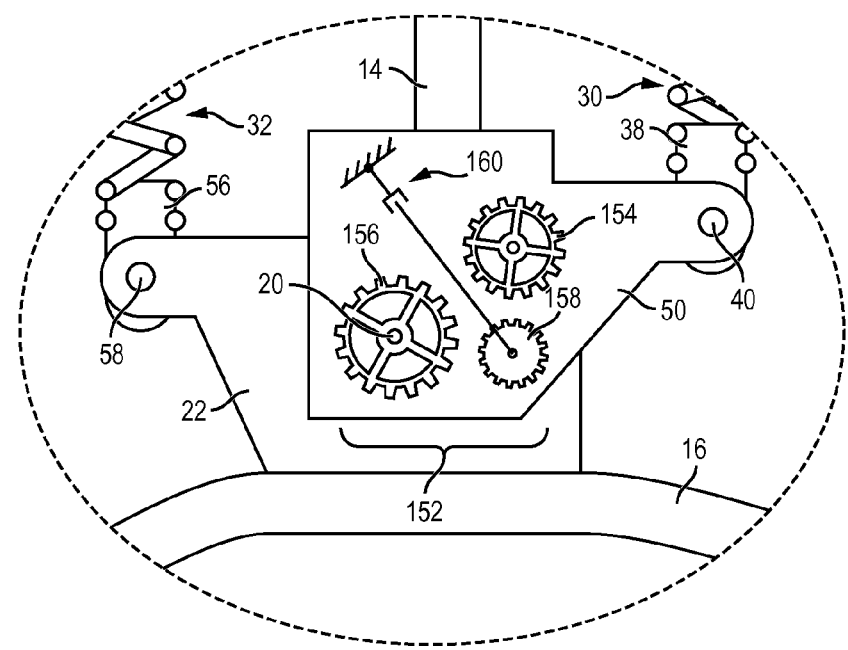

FIG. 5b shows an alternative clutch for joint system 10. Clutch 50 includes a gear system 152 having one or more gears. Clutch gear 154 is fixed on a housing of clutch 50. Shaft gear 156 coupled to ankle joint 20. Clutch gear 154 and shaft gear 156 are configured to engage and disengage through interface gear 158. Interface gear 158 is coupled to an actuator 160, which controls a position of interface gear 158. Actuator 160 may comprise an electric motor and lead screw, hydraulic, pneumatic, rotary, direct-drive, series-elastic, electroactive polymer-based, chemical-based, or other actuation scheme. Actuator 160 is a low power motor, such as a 20 W motor. Actuator 160 moves interface gear 158 between a locked and unlocked position. By positioning interface gear 158 in a locked position, clutch 50 locks with respect to foot mounting block 22 and main body 14. In another embodiment, clutch gear 154, shaft gear 156, and interface gears 158 are smooth friction wheels that have no gear teeth.

Figure 5C:
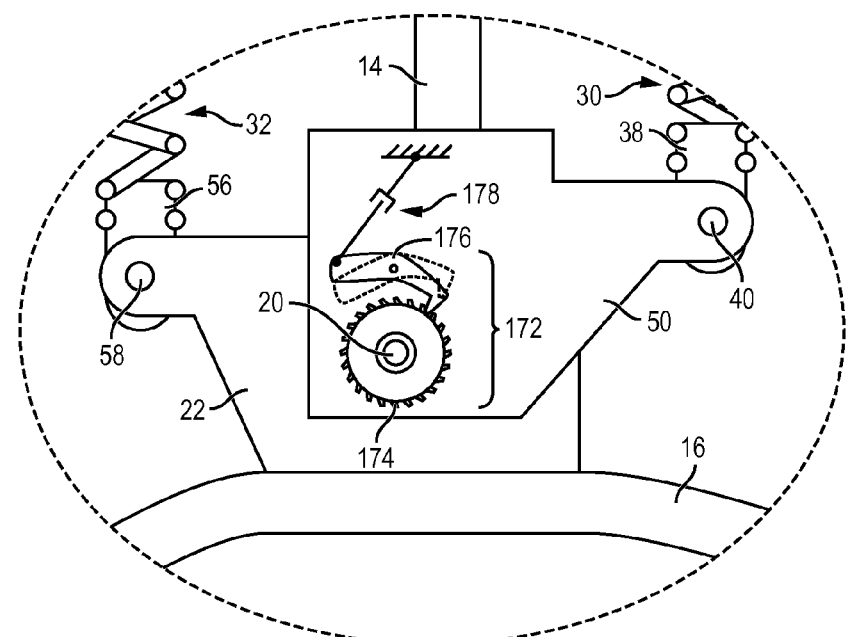

FIG. 5c shows an alternative clutch for joint system 10. Clutch 50 includes a gear and pawl system 172. Gear and pawl system 172 includes a gear 174 coupled to ankle joint 20 and further includes a pawl 176. Gear 174 is configured to interface with pawl 176 to lock clutch 50. Pawl 176 is coupled to an actuator 178, which controls a position of pawl 176. Actuator 178 may comprise an electric motor and lead screw, hydraulic, pneumatic, rotary, direct-drive, series-elastic, electroactive polymer-based, chemical-based, or other actuation scheme. Actuator 178 is a low power motor, such as a 20 W motor. Actuator 178 controls a position of pawl 176. By positioning pawl 176 in a locked position, clutch 50 locks with respect to foot mounting block 22 and main body 14.

Figure 5D:
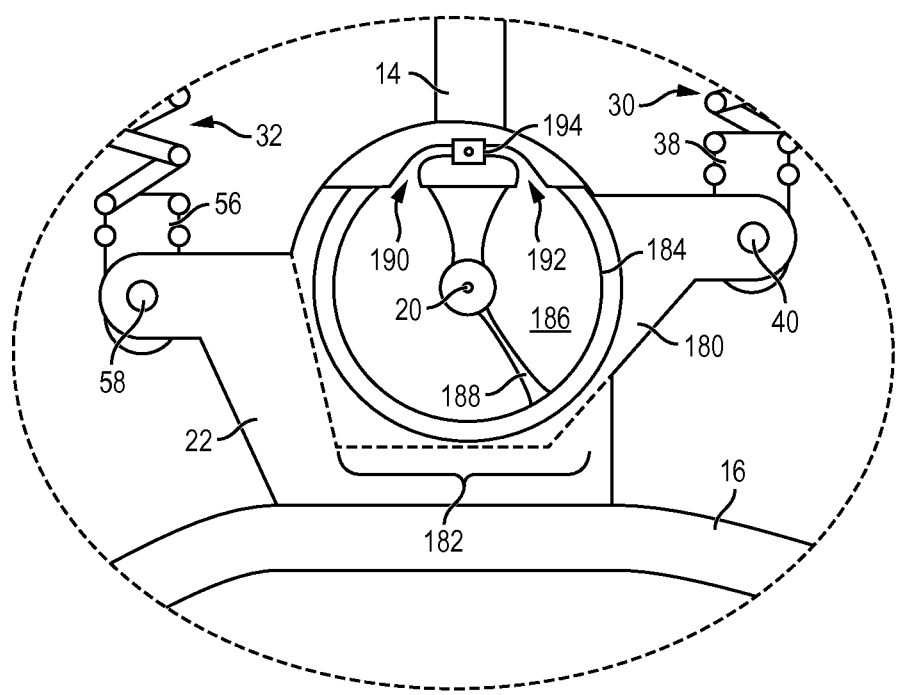

FIG. 5d shows an alternative clutch for joint system 10. Clutch 180 includes a rotary vane damper 182. Rotary vane damper 182 operates as a hydraulic or pneumatic valve. Rotary vane damper 182 includes a reservoir 184 filled with air or other lightweight fluid 186. Rotary vane damper 182 includes a vane 188 and ports 190 and 192 disposed on opposing sides of vane 188. A valve 194 is disposed between ports 190 and 192 to control the flow of fluid 186. Valve 194 is controlled by a low power actuator, which opens and closes valve 194. In the open position, valve 194 allows fluid 186 to recirculate or to exhaust. Vane 188 is free to move within reservoir 184 as clutch 180 rotates about ankle joint 20. Clutch 180 unlocks and is free to rotate with respect to foot mounting block 22 and main body 14. In the closed position, valve 194 prevents fluid 186 from circulating and vane 188 does not rotate. Clutch 180 locks with respect to foot mounting block 22 and main body 14.

Figure 6A:
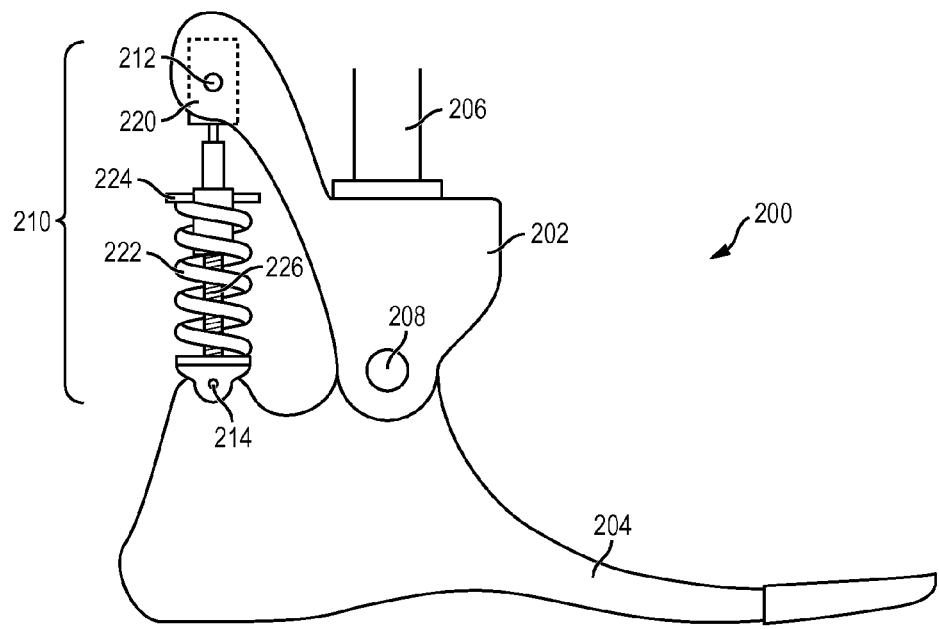
FIGS. 6a-6b illustrate an alternative quasi-active ankle device including a variable stiffness spring.
Figure 6B:
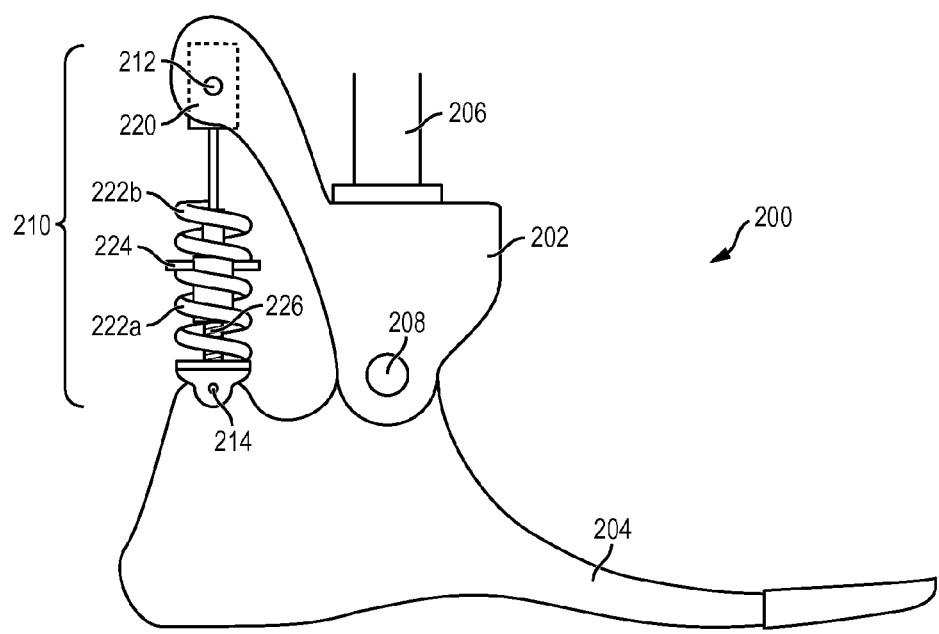

FIGS. 6a-6b show an alternative quasi-active ankle device including a variable stiffness spring. FIG. 6a shows prosthetic ankle device 200. Prosthetic ankle device 200 operates as a quasi-active prosthetic device or wearable robotic device including active and passive components. In one embodiment, prosthetic ankle device 200 is a below-the-knee prosthesis, which is also commonly known as a foot-ankle prosthesis or ankle prosthesis. In another embodiment, prosthetic ankle device 200 includes a robotic or prosthetic joint, such as a knee joint, hip joint, or other joint. Prosthetic ankle device 200 is worn by a user to replace a missing lower limb and restore the user's mobility and gait.

Prosthetic ankle device 200 includes a main body 202 and a foot portion or foot 204. Main body 202 couples to shank 206. Shank 206 is configured to couple to a socket, which fits onto a residual limb of a user. Foot 204 couples to main body 202 at an ankle joint 208. In one embodiment, ankle joint 208 includes a revolute or cylindrical joint and provides one degree of freedom by allowing rotation in the sagittal plane. In another embodiment, ankle joint 208 includes one or more joint types, or combination of joint types, such as revolute, prismatic, screw, spherical, planar, cylindrical, rigid, or other joint types, to provide one or more degrees of freedom at ankle joint 208.

Main body 202 is further coupled to foot 204 by spring-based actuator 210. Spring-based actuator 210 is coupled to main body 202 at joint 212. Spring-based actuator 210 is coupled to foot 204 at joint 214. Spring-based actuator 210 operates as a linking arm between joints 212 and 214. In one embodiment, spring-based actuator 210 is disposed behind the ankle, or in a posterior position with respect to ankle joint 208. In another embodiment, spring-based actuator 210 is disposed in an anterior position with respect to ankle joint 208.

Spring-based actuator 210 includes a mechanical element based upon the concept of adding and subtracting active coils from a helical spring. In one embodiment, spring-based actuator 210 includes a JackSpring™ Actuator, which further is described in U.S. Pat. Nos. 7,992,849 and 8,322,695, entitled Adjustable Stiffness Jack Spring Actuator, the entire disclosures of which are incorporated herein by reference. In another embodiment, spring-based actuator 210 includes any compliant actuator, spring-based actuator, or adjustable spring-based actuator.

Spring-based actuator 210 includes an actuator 220 disposed in series with a spring 222. Spring 222 includes a helical or coil spring. Spring 222 includes active coils and inactive coils defined by a nut 224. Active coils are coils that are available in the system to engage in compression or extension. Inactive coils are coils that are not available to the system to engage in compression or extension. The number of active and inactive coils is changed dynamically by actuator 220. Changing the number of active and inactive coils available in spring 222 changes the stiffness of spring 222.

Nut 224 is coupled to an actuator arm 226. In one embodiment, actuator 220 includes a lead screw motor and actuator arm 226 includes a threaded screw. In one embodiment, actuator 220 rotates spring 222 to add or subtract active coils. In another embodiment, actuator 220 causes nut 224 to translate along actuator arm 226 to add or subtract active coils. Nut 224 travels along the length of actuator arm 226 to change the number of active coils in spring-based actuator 210. Thus, the number of active coils is defined by a position of spring actuation nut 224 with respect to spring 222. Spring-based actuator 210 dynamically changes the number of active coils to drive tension or compression into or out of spring 222. As a result, spring 222 operates as a variable stiffness spring. The stiffness of spring 222 is selected to control the moment produced at ankle joint 208.

FIG. 6b, shows spring-based actuator 210 in a second position. Nut 224 is translated down actuator arm 226 toward joint 214. In one embodiment, active coils 222a are disposed between nut 224 and joint 214 and inactive coils 222b are disposed between nut 224 and actuator 220. In another embodiment, spring-based actuator 210 is arranged such that active coils 222a couple to another joint of prosthetic ankle device 200. Inactive coils 222b are shown in a position opposite spring actuation nut 224 from active coils 222a. During the loading phase of a gait cycle, spring-based actuator 210 holds a position. Nut 224 is configured to be non-backdrivable along actuator arm 226, such that external forces on spring 222 and nut 224 will not cause nut 224 to translate along actuator arm 226. In the case that the system builds up too much torque at ankle joint 208, energy is released at a controlled rate to dissipate some of the energy stored in primary spring 30. By driving the nut 224 along actuator arm 226 while spring 222 is loaded, energy stored in spring 222 is dissipated.

At the toe off phase of the gait cycle, actuator 220 engages to translate nut 224 to increase the number of active coils 222a. By increasing the number of active coils 222a, the toe of foot 204 is lifted for swing phase. At or just before heel strike, actuator 220 engages to translate nut 224 to a starting position to reset the number of active coils 222a according to the desired stiffness of spring 222. The stiffness of spring 222 is selected to absorb the force of heel strike. Alternatively, actuator 220 controls rate of translation of nut 224 during heel strike. The number of active coils 222a is reset to a starting position just before or at the time the heel of foot 204 makes contact with the ground.

Figure 7A:
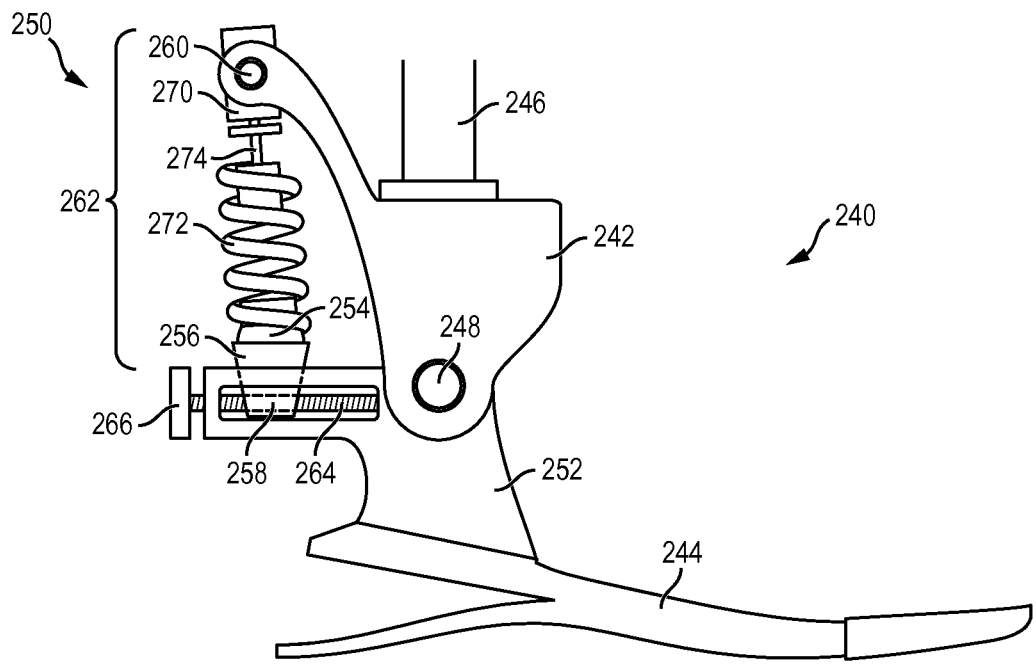
FIGS. 7a-7b illustrate an alternative quasi-active ankle device including a variable length lever arm.
Figure 7B:
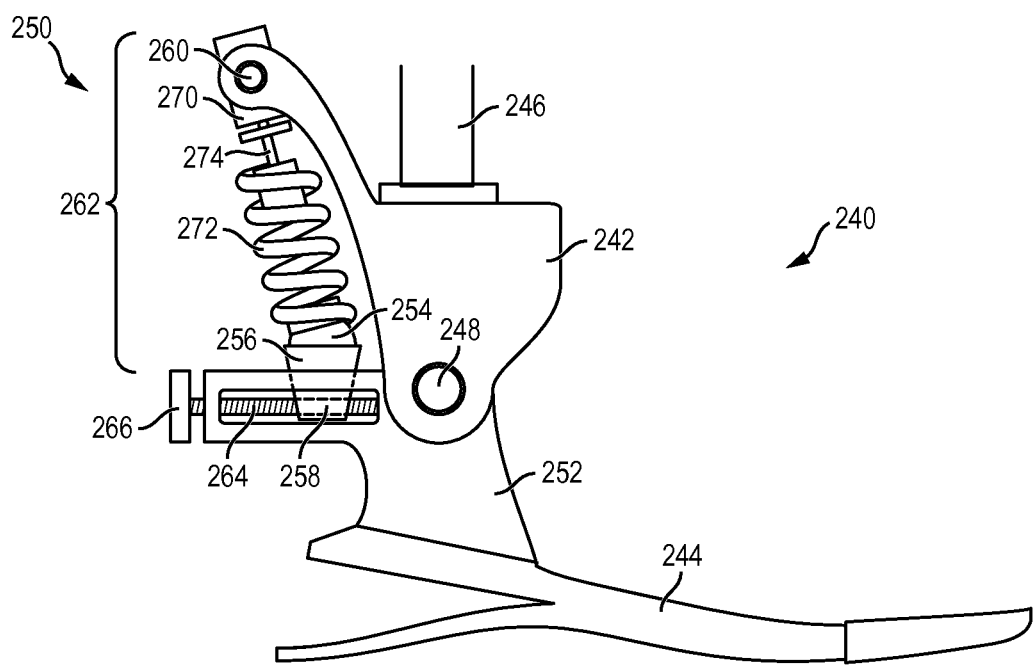

FIGS. 7a-7b show an alternative quasi-active ankle device including a variable length lever arm. FIG. 7a shows prosthetic ankle device 240 including a variable length lever arm in a first position. Prosthetic ankle device 240 operates as a quasi-active prosthetic device or wearable robotic device including active and passive components. In one embodiment, prosthetic ankle device 240 is a below-the-knee prosthesis, which is also commonly known as a foot-ankle prosthesis or ankle prosthesis. In another embodiment, prosthetic ankle device 240 includes a robotic or prosthetic joint, such as a knee joint, hip joint, or other joint. Prosthetic ankle device 240 is worn by a user to replace a missing lower limb and restore the user's mobility and gait.

Prosthetic ankle device 240 includes a main body 242 and a foot portion or foot 244. Main body 242 couples to shank 246. Shank 246 is configured to couple to a socket, which fits onto a residual limb of user 90. Foot 244 couples to main body 242 at an ankle joint 248. In one embodiment, ankle joint 248 includes a revolute or cylindrical joint and provides one degree of freedom by allowing rotation in the sagittal plane. In another embodiment, ankle joint 248 includes one or more joint types, or combination of joint types, such as revolute, prismatic, screw, spherical, planar, cylindrical, rigid, or other joint types, to provide one or more degrees of freedom at ankle joint 248.

Main body 242 is coupled to foot 244 by joint system 250. Joint system 250 operates as a variable lever arm system. A foot mounting block 252 couples joint system 250 to ankle joint 248 and foot 244. Foot 244 is rigidly affixed to foot mounting block 252. Main body 242 rotates at ankle joint 248 with respect to foot mounting block 252 and foot 244. Joint system 250 is coupled to foot mounting block 252 at joint 254 of a lever arm mount 256. Joint 254 includes a revolute, prismatic, screw, spherical, planar, cylindrical, rigid, or other joint types. Lever arm mount 256 is coupled to foot mounting block 252 at joint 258. In one embodiment, joint 258 is manually adjusted to adjust the length of the lever arm of joint system 250. In another embodiment, joint 258 is controlled by an actuator to adjust the length of the lever arm of joint system 250. In another embodiment, joint 258 is controlled by a cam linked to ankle joint 248, such that the lever arm position changes as a function of the ankle angle.

Joint system 250 is coupled to main body 242 at joint 260. Joint 260 includes a revolute, prismatic, screw, spherical, planar, cylindrical, rigid, or other joint types. Joint system 250 includes a compliant actuator system 262. Compliant actuator system 262 of joint system 250 extends from joint 258 to joint 260. Lever arm mount 256 couples to lever arm 264 at joint 258. Lever arm mount 256 translates along lever arm 264 to adjust the effective length of lever arm 264. Adjustment link 266 controls the position of lever arm mount 256 and joint 258 along lever arm 264. The position of lever arm mount 256 determines the effective length of lever arm 264 and the torsional stiffness of joint system 250.

Joint system 250 includes an actuator 270 and spring 272 disposed in series between joints 254 and 260. Actuator 270 includes drive screw and nut 274, which operates to lock and unlock spring 272. Actuator 270 controls engagement and disengagement of spring 272. Actuator 270 is a low power motor, such as a 20 W motor. Actuator 270 optionally includes a braking element, such as a damper. During the loading phase of the gait cycle, actuator 270 is locked, preventing nut 274 from translating along the axis of actuator 270. Spring 272 stretches during the roll over of shank 246 over ankle joint 248. Energy is stored in the tension of spring 272. After toe-off, actuator 270 drives nut 274 into spring 272, which picks up the toe for ground clearance during swing phase. Therefore, actuator 270 is used to control the release of energy in spring 272 and also to provide toe lift. At or just before heel strike, actuator 270 drives nut 274 back to a starting position. Alternatively, actuator 270 controls rate of translation of nut 274 during heel strike until nut 274 is reset to a starting position.

FIG. 7b shows prosthetic ankle device 240 including a variable length lever arm in a second position. The position of lever arm mount 256 on lever arm 264 changes the length of lever arm 264 with respect to main body 242. The length of lever arm 264 is adjustable to control the stiffness of joint system 250. The torsional stiffness of joint system 250 is related to linear spring stiffness of spring 272 and the length of lever arm 264. Therefore, changing position of lever arm mount 256 on lever arm 264 has the effect of changing the torsional stiffness of the device. The position of lever arm mount 256 is manually or automatically controlled by an actuator and control system. Controlling the length of lever arm 264 to control spring 272 stiffness allows prosthetic ankle device 240 to be tuned for a wide range of users. An automatically controlled lever arm 264 adapts to change the stiffness of the device while user changes gait activities. Prosthetic ankle device 240 also adapts to various terrains and slopes.

Figure 8A:
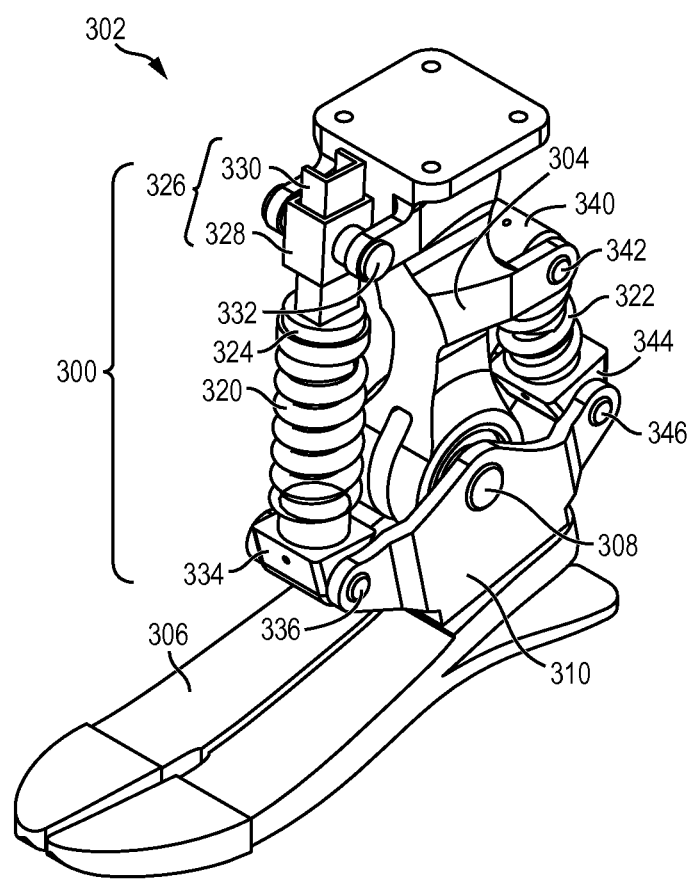
FIGS. 8a-8d illustrate prosthetic ankle devices including alternative clutch systems.

FIGS. 8a-8d show a quasi-active ankle device including alternative clutch systems. In FIG. 8a, a joint system 300 is implemented into a prosthetic ankle device 302. Prosthetic ankle device 302 operates as a quasi-active prosthetic device or wearable robotic device including active and passive components. Joint system 300 includes an active element, such as an actuator or motor, and passive components, such as springs and damping elements. Prosthetic ankle device 302 is similar to prosthetic ankle device 12 and includes joint system 300 for timing the engagement of compliant members. In one embodiment, prosthetic ankle device 302 is a below-the-knee prosthesis, which is also commonly known as a foot-ankle prosthesis or ankle prosthesis. In another embodiment, prosthetic ankle device 302 includes a robotic or prosthetic joint, such as a knee joint, hip joint, or other joint. Prosthetic ankle device 302 is worn by a user to replace a missing lower limb and restore the user's mobility and gait.

Prosthetic ankle device 302 includes a main body or pylon 304 and a foot portion or foot 306. Main body 304 is configured to couple to a socket, which fits onto a residual limb of a user. Foot 306 couples to main body 304 at an ankle joint 308 on foot mounting block 310. Foot mounting block 310 is rigidly coupled to foot 306. Foot mounting block 310 supports ankle joint 308. Ankle joint 308 comprises the primary joint for quasi-active joint system 300 and mimics a human ankle joint. Foot 306 rotates or pivots with respect to main body 304 at ankle joint 308. In one embodiment, ankle joint 308 includes a revolute or cylindrical joint and provides one degree of freedom by allowing rotation in the sagittal plane. In another embodiment, ankle joint 308 includes one or more joint types, or combination of joint types, such as revolute, prismatic, screw, spherical, planar, cylindrical, rigid, or other joint types, to provide one or more degrees of freedom at ankle joint 308.

Joint system 300 is configured to control the interface of main body 304 and foot 306 of prosthetic ankle device 302. Joint system 300 includes one or more compliant elements coupled to main body 304. In one embodiment, joint system 300 includes two or more compression springs, such as primary spring 320 and secondary spring 322. A primary spring 320 is coupled between main body 304 and foot 306 in a front or anterior position with respect to main body 304. A secondary spring 322 is coupled between main body 304 and foot 306 in a rear or posterior position with respect to main body 304. Primary spring 320 and secondary spring 322 are disposed in parallel between main body 304 and foot 306 on opposing sides of main body 304. Primary spring 320 is selected with a stiffness or spring constant that is greater than a stiffness or spring constant of secondary spring 322. Primary spring 320 is configured to absorb a substantial portion of the force of a gait step during stance phase and return the energy stored in primary spring 320 to the user during push off. Secondary spring 322 is configured to control the position of foot 306 during swing phase.

Primary spring 320 is coupled to main body 304 by spring mount 324 disposed at a first end of primary spring 320. Spring mount 324 is coupled to main body 304 by a sliding joint 326. Sliding joint 326 includes a clutch 328 and a slider 330. Spring mount 324 is also coupled to main body 304 by a joint 332. Primary spring 320 is coupled to ankle joint 308 by spring mount 334 at a second end of primary spring 320 opposite the first end. Spring mount 334 couples primary spring 320 to foot mounting block 310 at joint 336. In one embodiment, joints 332 and 336 include rigid joints. In another embodiment, joints 332 and 336 include revolute or cylindrical joints and permit primary spring 320 to pivot or rotate in the sagittal plane.

Secondary spring 322 is coupled to main body 304 by spring mount 340 at a first end of secondary spring 322. Spring mount 340 couples secondary spring 322 to main body 304 at joint 342. Secondary spring 322 is coupled to foot 306 by spring mount 344 at a second end of secondary spring 322 opposite the first end. Spring mount 344 couples secondary spring 322 to foot 306 at joint 346. In one embodiment, joints 342 and 346 include rigid joints. In another embodiment, joints 342 and 346 include revolute or cylindrical joints and permit secondary spring 322 to pivot or rotate in the sagittal plane. Foot mounting block 310 is rigidly coupled to foot 306. Therefore, joint system 300 is coupled between main body 304 and foot 306 and spans ankle joint 308.

Figure 8B:
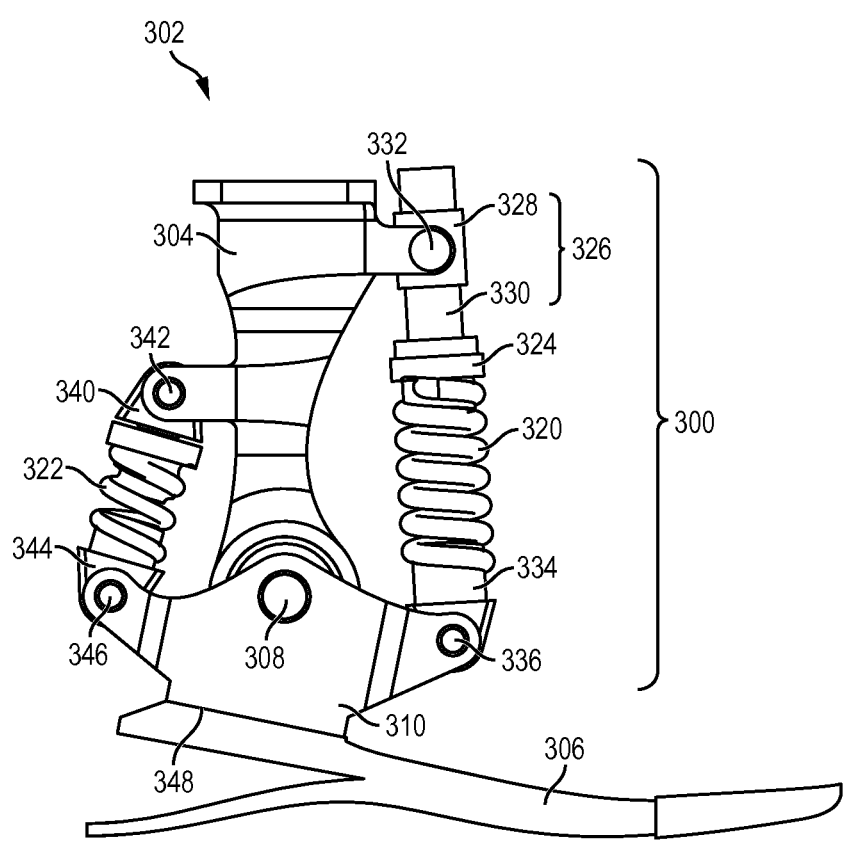

FIG. 8b shows a side view of prosthetic ankle device 302 including joint system 300. Main body 304 comprises the primary shaft of joint system 300. Main body 304 is a rigid member that acts on primary spring 320 and secondary spring 322 to deflect the springs. Main body 304 includes metal, metal alloy, polymer, fiberglass, carbon fiber, a composite material, or a natural material. Main body 304 may include additional compliant or damping members. For example, main body 304 may comprise a pylon and spring or a pylon with a spring and damper.

Foot 306 is a passive member and may include compliant features, such as a leaf spring. Foot 306 includes metal, metal alloy, polymer, fiberglass, carbon fiber, composite, or a natural material. Foot mounting block 310 is coupled to or integrated with foot 306. In one embodiment, foot mounting block 310 is coupled to foot 306 by a rigid joint 348. Foot mounting block 310 couples to main body 304 at ankle joint 308. Foot mounting block 310 couples to primary spring 320 at ankle joint 308 and to secondary spring 322 at joint 346.

Main body 304 interfaces with foot mounting block 310 through one or more bearings. Bearings may include radial bearings, ball bearings, thrust bearings, spherical or cylindrical ball bearings, or other bearing type. Main body 304, bearings, and foot mounting block 310 rotate about ankle joint 308 in the sagittal plane. In an alternative embodiment, ankle joint 308 is lockable and is controlled by a clutch. When ankle joint 308 is unlocked, main body 304 rotates relative to foot 306. When ankle joint 308 is locked, main body 304 is locked in a fixed position with respect to foot 306 and foot mounting block 310 such that main body 304 and foot 306 move together.

Primary spring 320 and secondary spring 322 are disposed on opposing sides of ankle joint 308. Primary spring 320 is disposed anterior to main body 304 and secondary spring 322 is disposed posterior to main body 304. In an alternative embodiment, the positions of primary spring 320 and secondary spring 322 are reversed and the posterior spring is the stiffer primary spring while the anterior spring is the softer secondary spring. In either configuration, the stiffer spring is the primary clutch-controlled spring.

Primary spring 320 is coupled to a fixed point on main body 304, such as a rigid flange of main body 304. The position of joint 332 on main body 304 is selected according to the desired behavior of primary spring 320. The distance between joint 332 and joint 336 relative to main body 304 determines the linear extension and compression behavior of primary spring 320 as well as the torsional behavior as primary spring 320 bends. Primary spring 320 is oriented between main body 304 and foot 306 and spans ankle joint 308 to compress and absorb energy as main body 304 rotates anteriorly over foot 306. Primary spring 320 is selected with a stiffness that supports the force generated during stance phase of gait. In one embodiment, primary spring 320 includes a helical or coil spring having a stiffness of 200,000 N/m. Primary spring 320 also bends with respect to the axis of the coil thereby operating as a torsional spring as well as a compression and tension spring. In another embodiment, primary spring 320 includes one or more helical or coil springs, torsional springs, leaf springs, or other compliant members. Additional linking members, such as a damping element, may be disposed in parallel or in series with primary spring 320. The operation of primary spring 30 is controlled by sliding joint 326.

Sliding joint 326 is a linking member that couples primary spring 320 to main body 304. Sliding joint 326 comprises a prismatic linking member or prismatic joint, similar to prismatic joint 124 in FIGS. 2e-2d. Sliding joint 326 controls engagement and disengagement of primary spring 320. In one embodiment, slider 330 is controlled by an actuator, which is controlled by control system 100. In another embodiment, sliding joint 326 includes a passive mechanical locking mechanism. When sliding joint 326 is in a locked position, primary spring 320 is engaged. When sliding joint 326 is in an unlocked position, primary spring 320 is disengaged. By controlling the timing of the engagement of primary spring 320 according to the user's gait dynamics determined from sensor 96, the energy stored in primary spring 320 can be released at selected timing and selected release rates for more efficient use of the passive energy stored in primary spring 320.

Secondary spring 322 is coupled to a fixed point on main body 304, such as a rigid flange of main body 304. Secondary spring 322 is further coupled to a fixed point on foot mounting block 310, such as a rigid flange of foot mounting block 310. Secondary spring 322 spans ankle joint 308. The positions of joint 342 on main body 304 and joint 346 on foot mounting block 310 are selected according to the desired behavior of secondary spring 322. The distance between joint 342 and joint 346 relative to main body 304 determines the linear extension and compression behavior of secondary spring 322 as well as the torsional behavior as secondary spring 322 bends.

Secondary spring 322 is oriented between main body 304 and foot 306 to control the plantarflexion and dorsiflexion of foot 306. Secondary spring 322 is configured to be engaged during the entire gait cycle and does not require a clutch or locking mechanism. Secondary spring 322 is selected with a stiffness that is less than the stiffness of primary spring 320, but with a stiffness great enough to control foot 306. In one embodiment, secondary spring 322 includes a helical or coil spring having a stiffness of 45,000 N/m. Secondary spring 322 also bends with respect to the axis of the coil thereby operating as a torsional spring as well as a compression and tension spring. In another embodiment, secondary spring 322 includes one or more helical or coil springs, torsional springs, leaf springs, or other compliant members. Additional linking members, such as a damping element, may be disposed in parallel or in series with secondary spring 322.

In another embodiment, secondary spring 322 is clutch-controlled and secondary spring 322 is engaged and disengaged at controlled points during the gait cycle. By timing of the engagement and disengagement of secondary spring 322, the timing for toe lift is modulated. The timing of the engagement of either or both of primary spring 320 and secondary spring 322 is controlled by an actuator and results in a quasi-active joint system. In the quasi-active embodiment, sliding joint 326 is locked and unlocked by an actuator, such as actuator 104, controlled by control system 100. During the loading phase of the gait cycle, sliding joint 326 is locked and operates as a rigid joint. Slider 330 is fixed with respect to clutch 328 and main body 304, and primary spring 320 is engaged. During swing phase of the gait cycle, sliding joint 326 is unlocked and operates as a prismatic joint. Slider 330 translates with respect to clutch 328 and main body 304, and primary spring 320 is disengaged.

Alternatively, sliding joint 326 is controlled by a passive mechanical system. In the passive embodiment, sliding joint 326 is locked and unlocked by a mechanical system. During swing phase, sliding joint 326 is unlocked. As heel strike, the weight of user 90 provides a force, which pushes down on secondary spring 322. Secondary spring 322 provides shock absorption to allow user 90 to feel a normal step. As main body 304 begins to rollover ankle joint 308 to reach the neutral position, slider 330 moves with respect to clutch 328 and turns a gear piece within sliding joint 326 that locks into place. Once sliding joint 326 is locked, primary spring 320 is engaged. As main body 304 continues to rollover ankle joint 308 passed the neutral position, slider 330 pushes down on primary spring 320, compressing and increasing the potential energy in primary spring 320. Secondary spring 322 is engaged and forced into tension. At toe off, primary spring 320 and secondary spring 322 want to return to neutral positions. Primary spring 320 extends, pushing foot 306 into toe off. Secondary spring 322 pulls on the heel of foot 306 while trying to compress. Both springs work together as joint system 300 returns to a neutral position and the toe lifts off the ground, returning energy stored in the springs back to the user. Secondary spring 322 neutral position is in a slightly dorsiflexed position. After toe off, secondary spring 322 acts to move foot 306 to a dorsiflexed position, raising slider 330. As slider 330 moves upward with respect to clutch 328, the gear piece within sliding joint 326 unlocks, releasing slider 330 and disengaging the primary spring 320.

In yet another embodiment, secondary spring 322 is optional, and joint system 300 includes a single spring, such as primary spring 320. Rather than a second spring, an actuator is used to position foot 306 during swing phase. The actuator returns primary spring 320 to a neutral position or zero torque position. The position of foot 306 is actively controlled to modulate the storage and release of energy during the gait cycle. Therefore, the benefits of timed energy release and efficient use of passive energy are achieved in joint system 300.

Figure 8C:
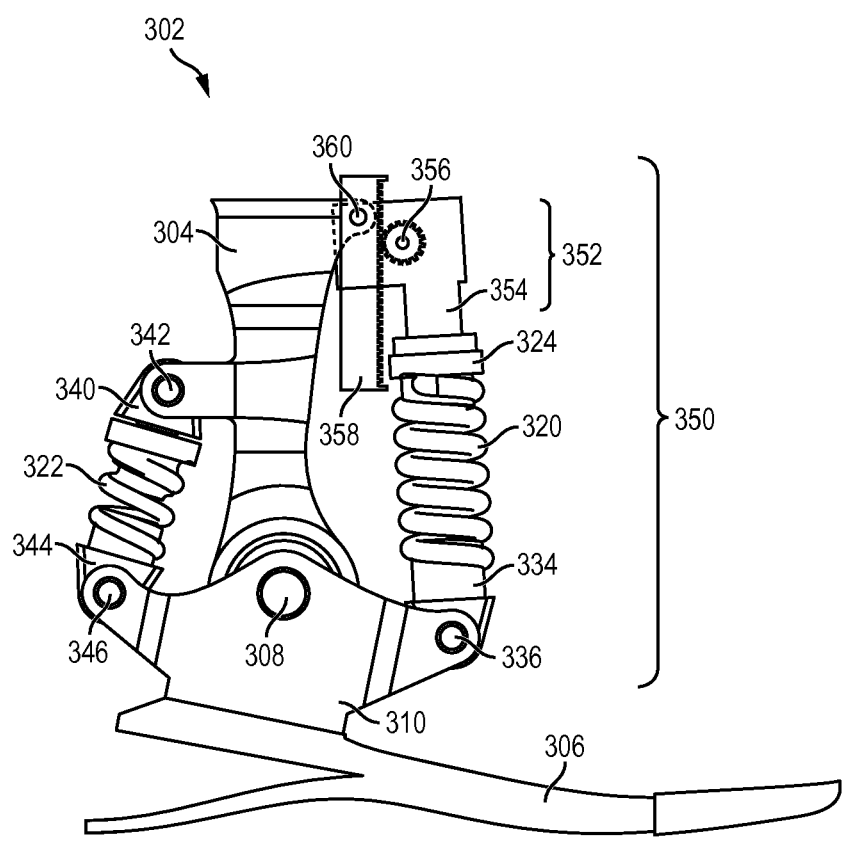

FIG. 8c shows a prosthetic ankle device 302 including an alternative sliding clutch. Prosthetic ankle device 302 includes joint system 350 including a clutch 352. Clutch 352 includes a rack and pinion system for controlling prosthetic ankle device 302. Slider 354 is coupled to pinion gear 356, which interfaces with rack 358. Rack 358 is coupled to main body 304 at joint 360, which includes a revolute joint or a rigid joint. Rack 358 and pinion gear 356 operate as a clutch-controlled prismatic joint. Pinion gear 356 is locked and unlocked by an actuator, such as actuator 104, controlled by control system 100. During the loading phase of the gait cycle, pinion gear 356 of clutch 352 is locked and operates as a rigid joint. Pinion gear 356 is fixed with respect to rack 358 and main body 304, and primary spring 320 is engaged. During swing phase of the gait cycle, pinion gear 356 is unlocked and rotates along rack 358, thereby translating slider 354. When unlocked, clutch 352 operates as a prismatic joint, and primary spring 320 is disengaged.

Figure 8D:
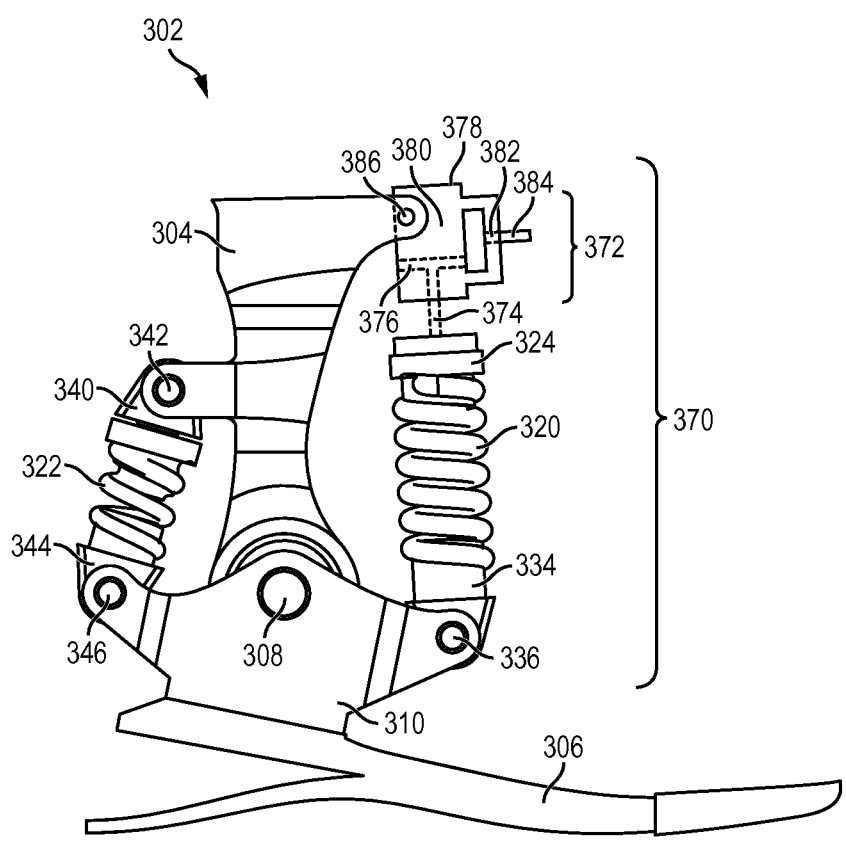

FIG. 8d shows a pneumatic or hydraulic clutch for controlling a quasi-active ankle device. Prosthetic ankle device 302 includes a joint system 370 including a clutch 372. Clutch 372 includes pneumatic or hydraulic linear clutch for controlling prosthetic ankle device 302. Slider or piston 374 couples to primary spring 320. Piston 374 is coupled to plunger 376, which is disposed within housing body 378. Housing body 378 contains fluid 380, such as air, oil, or other hydraulic fluid. Clutch 372 further includes a valve 382 for controlling the exhaust or recirculation of fluid 380. Valve 382 is controlled by an actuator 384. In the open position, valve 382 allows fluid 380 to recirculate in a hydraulic system, or valve 382 allows fluid 380 to exhaust in a pneumatic system. Valve 382 is free to move within housing body 378 and piston 374 operates as a prismatic joint. In the closed position, valve 382 prevents fluid 380 from circulating and piston 374 is locked in a fixed position. Primary spring 320 is engaged when valve 382 is in the closed position. Clutch 372 couples to main body 304 at joint 386, which includes a revolute joint.

Figure 9A:
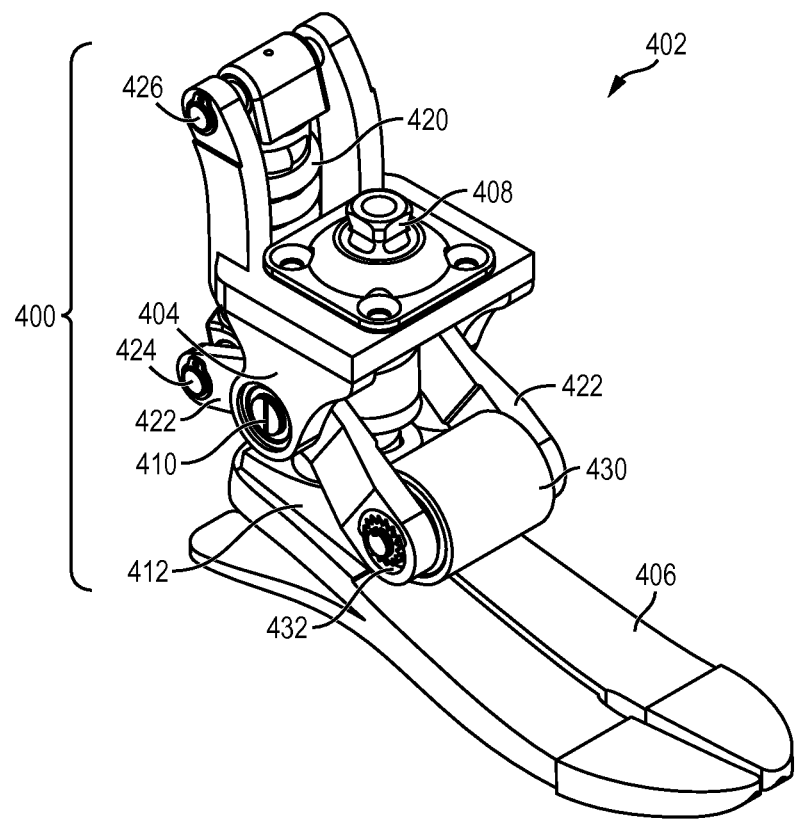
FIGS. 9a-9d illustrate a prosthetic ankle device including a passive clutch for timed power release.

FIGS. 9a-9d show a passive prosthetic design. In FIG. 9a, a joint system 400 is implemented into a prosthetic ankle device 402. Prosthetic ankle device 402 operates as a passive prosthetic device. Joint system 300 includes passive components, such as springs and damping elements. Prosthetic ankle device 402 includes joint system 400 for timing the engagement of compliant members. In one embodiment, prosthetic ankle device 402 is a below-the-knee prosthesis, which is also commonly known as a foot-ankle prosthesis or ankle prosthesis. In another embodiment, prosthetic ankle device 402 includes a robotic or prosthetic joint, such as a knee joint, hip joint, or other joint. Prosthetic ankle device 402 is worn by a user to replace a missing lower limb and restore the user's mobility and gait.

Prosthetic ankle device 402 includes a main body or pylon 404 and a foot portion or foot 406. Main body 404 includes a shank connector 408 configured to couple to a socket, which fits onto a residual limb of a user. Foot 406 couples to main body 404 at an ankle joint 410 on foot mounting block 412. Foot mounting block 412 is rigidly coupled to foot 406. Foot mounting block 412 supports ankle joint 410. Ankle joint 410 comprises the primary joint for joint system 400 and approximates a human ankle joint. Foot 406 rotates or pivots with respect to main body 404 at ankle joint 410. In one embodiment, ankle joint 410 includes a revolute or cylindrical joint and provides one degree of freedom by allowing rotation in the sagittal plane. In another embodiment, ankle joint 410 includes one or more joint types, or combination of joint types, such as revolute, prismatic, screw, spherical, planar, cylindrical, rigid, or other joint types, to provide one or more degrees of freedom at ankle joint 410.

Joint system 400 includes one or more compliant elements coupled to main body 404. In one embodiment, joint system 400 includes one or more compression springs, such as spring 420. Spring 420 is coupled between main body 404 and foot 420 in a posterior position with respect to main body 404. Spring 420 is configured to absorb a substantial portion of the force of a gait step during stance phase and return the energy stored in spring 420 to the user during push off. Spring 420 is coupled to ankle joint 410 by lever 422. Lever 422 couples to spring 420 at joint 424 at a first end of spring 420. Spring 420 is coupled to main body 404 at joint 426 at a second end of spring 420 opposite the first end. The timing of engagement of spring 420 is controlled by clutch 430. Clutch 430 is engaged and released by the loading and unloading of pylon 408 and though a mechanical one-way bearing 432.

Figure 9B:
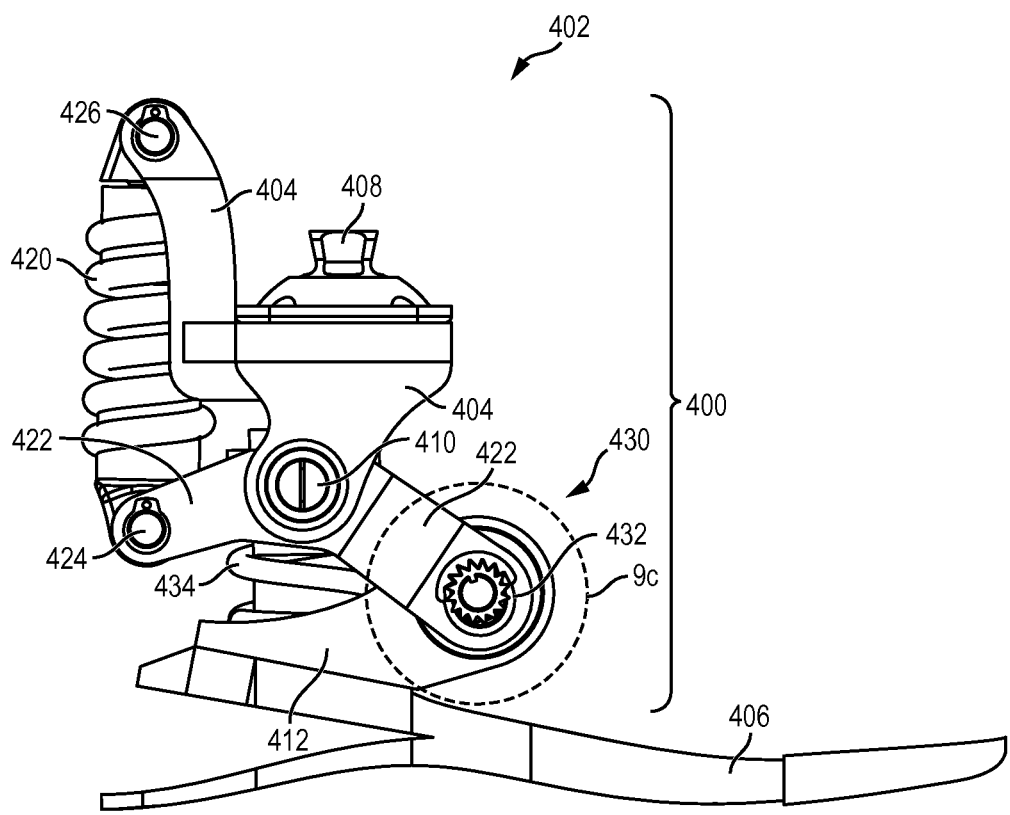

FIG. 9b shows a side view of prosthetic ankle device 402 with joint system 400. Main body 404 further includes pylon spring 434. Spring 420 is coupled to main body 404 and lever 422. During the loading phase of the gait cycle, clutch 430 is locked and operates as a one-way revolute joint. In one embodiment, the one-way revolute joint of clutch 430 allows plantarflexion, but not dorsiflexion, of the foot. The position of lever 422 is locked during the loading phase while main body 404 moves in dorsiflexion with respect to foot 406. Main body 404 and spring 420 are engaged as main body 404 dorsiflexes. During swing phase of the gait cycle, clutch 430 is unlocked and operates as a revolute joint. Lever 422 is free to rotate with respect to foot mounting block 412 and spring 420 is disengaged.

Figure 9C:
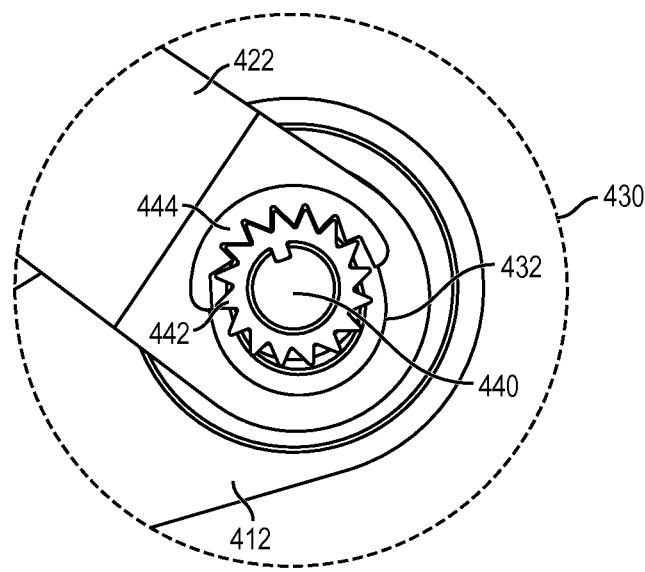

FIG. 9c shows clutch 430 of joint system 400 in further detail. In FIG. 9c, clutch 430 is shown in a locked position. Clutch 430 includes a shaft 440 including gear teeth 442 or other gear mechanism such as a friction gear. Clutch 430 further includes gear 444 coupled to lever 422. At heel strike, the weight of user 90 provides a force, which pushes down on lever 422. Lever 422 and gear 444 are pushed downward onto shaft 440. Gear 444 engages with gear teeth 442 to lock shaft 440. Gear 444 and gear teeth 442 engage mechanical one-way bearing 432 permitting movement of lever 422 in a counter-clockwise direction with respect to the view in FIG. 9c, which correlates to plantarflexion. Lever 422 is locked with respect to foot mounting block 412. When gear 444 engages with gear teeth 442 to lock shaft 440, main body 408 moves relative to lever 422 and foot mounting block 412. Spring 420 is engaged in tension as the user moves through the loading phase of gait.

Figure 9D:
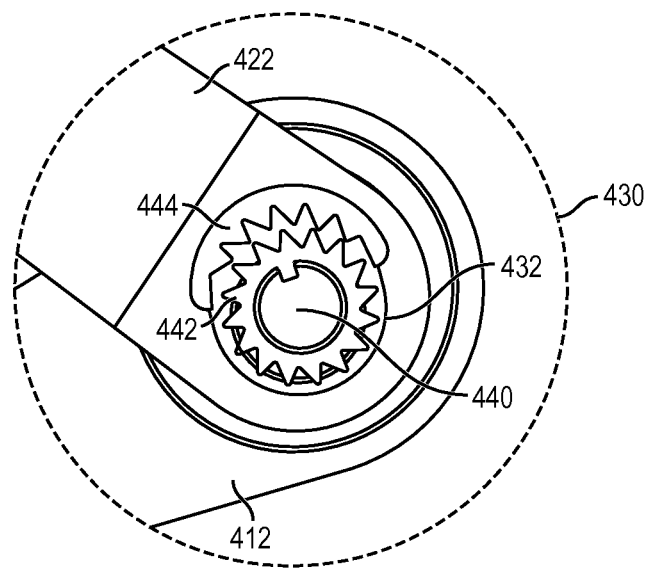

FIG. 9d shows clutch 430 of joint system 400 disengaged. At push off, the weight of user 90 is released from lever 422. Shaft 440 disengages from gear 444 and lever 422 rotates freely with respect to foot mounting block 412. Spring 420 is disengaged allowing spring 434 to return foot 406 to a neutral position in preparation for the next step.

Figure 10:
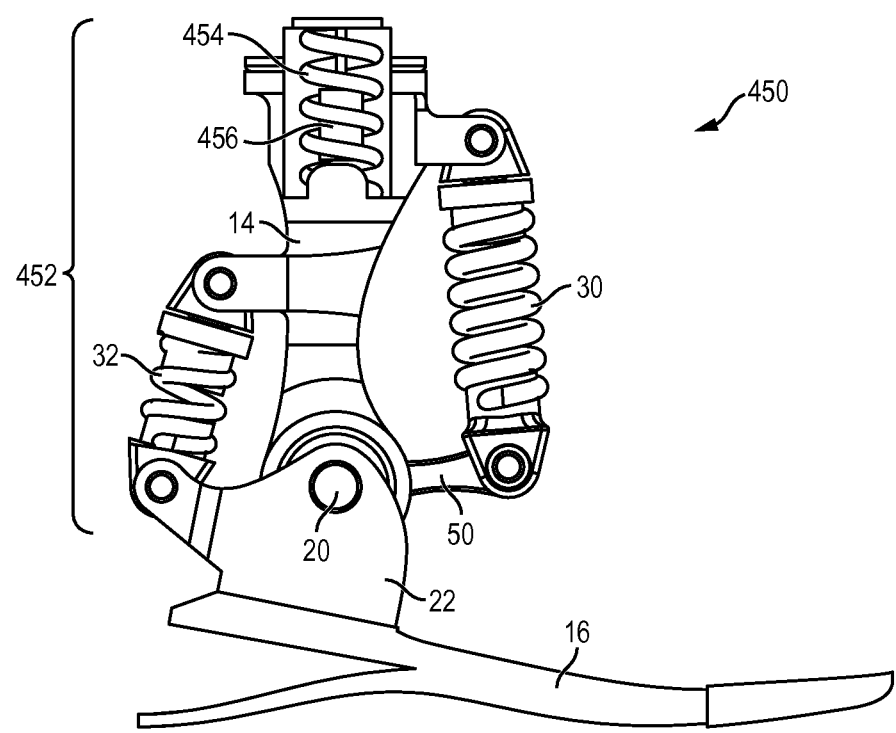
FIG. 10 illustrates an alternative prosthetic ankle device.

FIG. 10 shows prosthetic ankle device 450 including a joint system 452. Prosthetic ankle device 450 is similar to prosthetic ankle device 12, but includes a pylon spring 454 and damper 456 disposed on main body 14. Alternatively, pylon spring 454 is disposed between main body 14 and foot 16.

Figure 11:
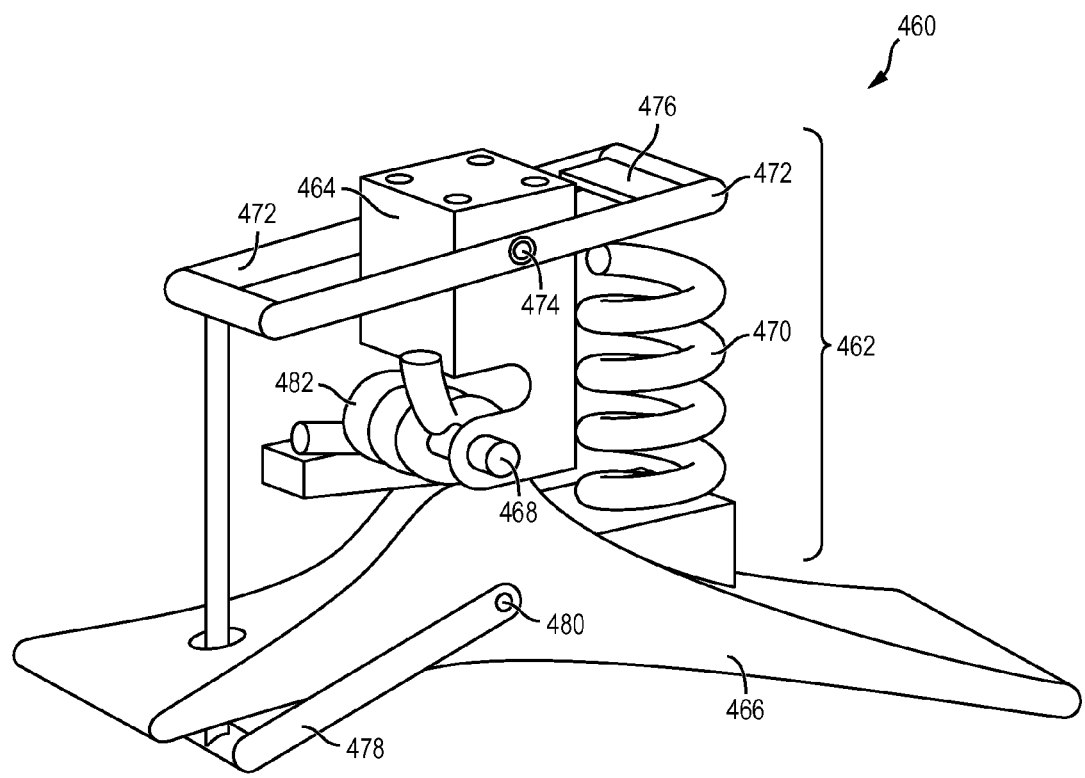
FIG. 11 illustrates an alternative prosthetic ankle device including a passive clutch.

FIG. 11 shows prosthetic ankle device 460 including a joint system 462. Prosthetic ankle device 460 includes a main body 464 and a foot portion or foot 466. Main body 464 is configured to couple to a socket, which fits onto a residual limb of a user. Foot 466 couples to main body 464 at an ankle joint 468. Main body 464 is further coupled to foot 466 through a spring 470 and upper lever 472. Upper lever 472 couples to main body at joint 474. Upper lever 472 interfaces with spring 470 at platform 476. Upper lever 472 is coupled to lower lever 478. Lower lever 478 is coupled to foot 466 at joint 480. Lower lever 478 controls the position of upper lever 472 and platform 476.

A torsional spring 482 is coupled between main body 464 and foot 466 at ankle joint 468. Spring 470 includes a linear spring and is coupled between main body 464 and foot 466 in a front or anterior position with respect to main body 464. Spring 470 is responsible for capturing and releasing the energy harnessed during roll over. Platform 476 is disposed above spring 470, with a gap disposed between spring 470 and platform 476. Torsional spring 482 is located at ankle joint 468. Torsional spring 482 is responsible for holding the toe in a raised position. Lower lever 478 is disposed on the bottom of the heel of foot 466. Lower lever 478 is pushed closed when the heel contacts the ground during stance phase. Lower lever 478 engages upper lever 472, which moves platform 476 down and closes the gap between platform 476 and spring 470. Spring 470 no longer has one free end and is therefore engaged. When the user steps forward, spring 470 is compressed, the energy of the rollover motion is stored in spring 470. The potential energy stored in spring 470 is then released once roll over is complete and heel rise begins. The energy released as spring 470 extends from a compressed state contributes to push off by assisting foot 466 in plantar-flexion. Lower lever 478 is disengaged when the user raises foot 466 and the gap between spring 470 and platform 476 opens. Torsional spring 482 raises the toe during swing phase.

Figure 12:
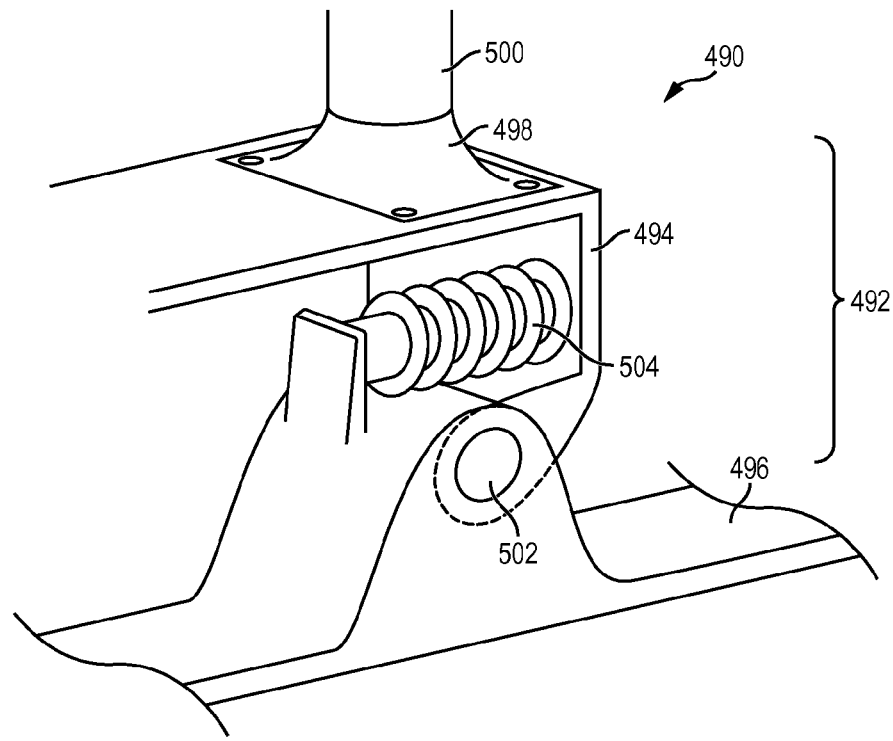
FIG. 12 illustrates a prosthetic ankle device including a torsional spring for toe lift.

FIG. 12 shows prosthetic ankle device 490 including a joint system 492. Prosthetic ankle device 490 includes a main body or pylon 494 and a foot portion or foot 496. Main body 494 includes a shank connector 498 is coupled to shank 500. Shank 500 is configured to couple to a socket, which fits onto a residual limb of a user. Foot 496 couples to main body 14 at an ankle joint 502. Spring 504 is coupled between main body 494 and foot 496. In one embodiment, spring 504 is a linear spring. Spring 504 is configured to assist foot 496 with toe rise during the swing phase of gait.

Figure 13:
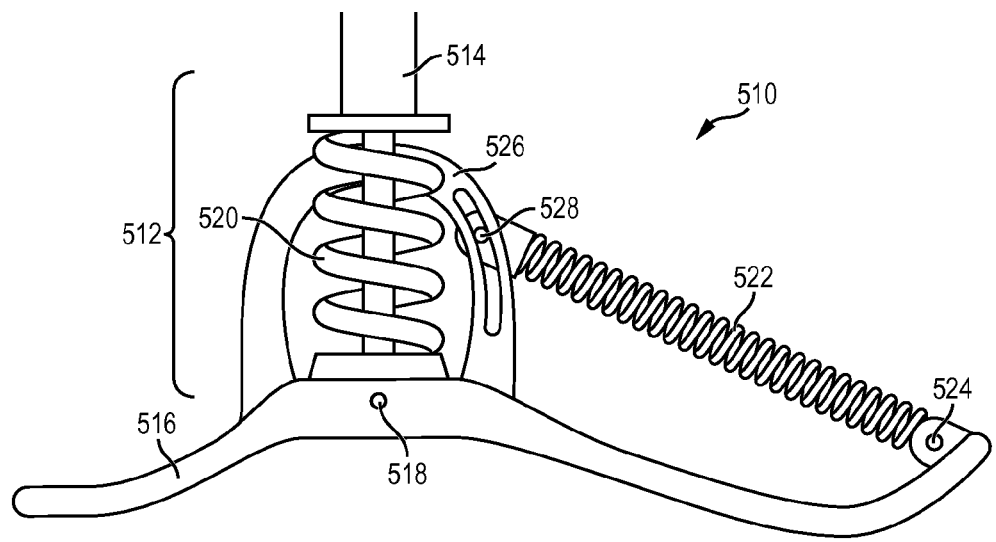
FIG. 13 illustrates a prosthetic ankle device including a sliding clutch.

FIG. 13 shows prosthetic ankle device 510 including a joint system 512. Joint system 512 includes springs and a slider configured to absorb the heel strike, store energy and help lift the toe. Prosthetic ankle device 510 includes a main body or pylon 514 and a foot portion or foot 516. Main body 514 is configured to couple to a socket, which fits onto a residual limb of a user. Foot 516 is coupled to main body 514 at an ankle joint 518. In one embodiment, ankle joint 518 includes a revolute or cylindrical joint and provides one degree of freedom by allowing rotation in the sagittal plane. Main body 514 rotates with respect to foot 516 at ankle joint 518.

A first spring 520 is coupled between main body 514 and foot 516. A second spring 522 is coupled between main body 514 and foot 516. Second spring 522 is coupled to foot 516 at joint 524. Second spring 522 is coupled to main body 514 through connector 526. Second spring 522 is coupled to connector 526 at joint 528. Joint 528 slides with respect to 526 to control the use of second spring 522. First spring 520 and second spring 522 work to absorb the heel strike, store energy and help lift the toe.

The joint systems described herein are employed in a variety of applications. The joint system can be applied to prosthetic, orthotic, or robotic devices that require control of joints for locomotion, and necessitate timed energy release of passive energy.

While one or more embodiments of the present invention have been illustrated in detail, the skilled artisan will appreciate that modifications and adaptations to those embodiments may be made without departing from the scope of the present invention as set forth in the following claims.

What is claimed:

1. A method of making a prosthetic joint device, comprising:
   providing a foot portion;
   providing a main body pivotally coupled to the foot portion at a first joint;
   providing a first compliant member coupled to the main body and foot portion;
   coupling a first clutch to the first compliant member;
   providing an actuator coupled to the first clutch to engage and disengage the first clutch; and
   disposing a second clutch on the first joint to lock and unlock the first joint.

2. The method of claim 1, further including locking the first clutch to engage the first compliant member.

3. The method of claim 1, further including providing a control system coupled to the actuator to control the actuator based on a gait activity.

4. The method of claim 1, further including coupling a second compliant member to the main body and foot portion.

5. The method of claim 4, further including:
   disposing the first compliant member on a first side of the first joint; and
   disposing the second compliant member on a second side of the first joint opposite the first side.

* * * * *